(12) United States Patent
Lee et al.

(10) Patent No.: US 10,087,472 B2
(45) Date of Patent: Oct. 2, 2018

(54) BIOLOGICAL SYNTHESIS OF 6-AMINOCAPROIC ACID AND TRANSGENIC MICROORGANISM THEREFOR

(71) Applicant: Korea Research Institute of Bioscience and Biotechnology, Daejeon (KR)

(72) Inventors: Hong-Weon Lee, Daejeon (KR); Jung Oh Ahn, Daejeon (KR); Joon Ki Jung, Daejeon (KR); Hee-Ju Ko, Daejeon (KR); Sun-Joo Park, Daejeon (KR); Chun Sug Kim, Daejeon (KR); Hyeok Won Lee, Daejeon (KR); Eun Gyo Lee, Daejeon (KR); Joo Hwan Lee, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 271 days.

(21) Appl. No.: 14/889,543

(22) PCT Filed: May 2, 2014

(86) PCT No.: PCT/KR2014/003933
§ 371 (c)(1),
(2) Date: Mar. 11, 2016

(87) PCT Pub. No.: WO2014/182016
PCT Pub. Date: Nov. 13, 2014

(65) Prior Publication Data
US 2016/0257976 A1    Sep. 8, 2016

(30) Foreign Application Priority Data

May 6, 2013  (KR) .......... 10-2013-0050676
May 2, 2014  (KR) .......... 10-2014-0053249

(51) Int. Cl.
*C12P 7/02* (2006.01)
*C12N 1/20* (2006.01)
(Continued)

(52) U.S. Cl.
CPC .......... *C12P 13/005* (2013.01); *C07D 223/10* (2013.01); *C12N 9/0008* (2013.01);
(Continued)

(58) Field of Classification Search
None
See application file for complete search history.

(56) References Cited

U.S. PATENT DOCUMENTS

2011/0171699 A1  7/2011  Raemakers-Franken et al.
2013/0017593 A1  1/2013  Baynes et al.

FOREIGN PATENT DOCUMENTS

JP    2011-515111 A    5/2011
JP    2013-515050 A    5/2013
(Continued)

OTHER PUBLICATIONS

International Search Report issued in corresponding International Patent Application No. PCT/KR2014/003933 dated Aug. 26, 2014.

*Primary Examiner* — Yong D Pak
(74) *Attorney, Agent, or Firm* — Morgan, Lewis & Bockius LLP

(57) ABSTRACT

The present invention relates to a method for preparing a recombinant microorganism simultaneously comprising genes encoding enzymes used in the biosynthesis pathway of 6-aminocaproic acid, which is a precursor of caprolactam, biosynthesizing 6-aminocaproic acid from the microorganism, and producing the same so as to synthesize caprolactam.

17 Claims, 16 Drawing Sheets

Specification includes a Sequence Listing.

(51) Int. Cl.
    *C12N 15/00*     (2006.01)
    *C12N 9/02*     (2006.01)
    *C12N 9/10*     (2006.01)
    *C12N 9/88*     (2006.01)
    *C07H 21/04*     (2006.01)
    *C12P 13/00*     (2006.01)
    *C07D 223/10*     (2006.01)
    *C12N 15/52*     (2006.01)
    *C12P 17/10*     (2006.01)

(52) U.S. Cl.
    CPC ......... *C12N 9/1029* (2013.01); *C12N 9/1096* (2013.01); *C12N 9/88* (2013.01); *C12N 15/52* (2013.01); *C12P 17/10* (2013.01)

(56) References Cited

FOREIGN PATENT DOCUMENTS

KR    10-2012-0034640 A    4/2012
WO       2012/177721 A1    12/2012

- 2-ketopimelic acid : control

- I-H+nemA

• positive control - 6-aminocaproic acid

• reaction

• negative control - empty vector

SEQUENCE LISTING

<160> NUMBER OF SEQ ID NOS: 36

<210> SEQ ID NO 1
<211> LENGTH: 789
<212> TYPE: DNA
<213> ORGANISM: Escherichia coli

<400> SEQUENCE: 1

```
atggaaaaca gttttaaagc ggcgctgaaa gcaggccgtc cgcagattgg attatggctg      60
gggctgagca gcagctacag cgcggagtta ctggccggag caggattcga ctggttgttg     120
atcgacggtg agcacgcacc gaacaacgta caaaccgtgc tcacccagct acaggcgatt     180
gcgccctatc ccagccagcc ggtagtacgt ccgtcgtgga cgatccggt gcaaatcaaa      240 caactgctgg acgtcggcac acaaaccttta ctggtgccga tggtacaaaa cgccgacgaa     300
gcccgtgaag cggtacgcgc cacccgttat cccccgccg gtattcgcgg tgtgggcagt      360
gcgctggctc gcgcctcgcg ctggaatcgc attcctgatt acctgcaaaa agccaacgat     420
caaatgtgcg tgctggtgca gatcgaaacg cgtgaggcaa tgaagaactt accgcagatt     480
ctggacgtgg aaggcgtcga cggcgtgttt atcggcccgg cggatctgag cgccgatatg     540
ggttatgccg gtaatccgca gcacccggaa gtacaggcc ccattgagca ggcgatcgtg      600
cagatccgcg aagcgggcaa agcgccgggg atcctgatcg ccaatgagct actggcaaaa     660
cgctatctgg aactgggcgc gctgtttgtc gccgtcggcg ttgacaccac cctgctcgcc     720
cgcgccgccg aagcgctggc agcacggttt ggcgcgcagg ctacagcgat taagcccggc     780
gtgtattaa                                                              789
```

<210> SEQ ID NO 2
<211> LENGTH: 804
<212> TYPE: DNA
<213> ORGANISM: Escherichia coli

<400> SEQUENCE: 2

```
atgttcgaca aacacaccca caccctgatc gcccagcgtc tggatcaggc agaaaaacag      60
cgcgaacaga tccgcgcgat ctcgctggat tacccggaga tcaccatcga agacgcttac    120
gcggtgcagc gtgaatgggt tcgactgaaa atcgccgaag tcgcacgct gaaaggccac     180 aaaatcggcc tgacctcgaa agcgatgcag gccagctcgc agatcagcga accggattac    240
```

```
ggtgcactgc tggacgacat gttcttccac gatggcagcg atatcccgac cgatcgcttt      300
atcgtgccgc gcattgaagt ggagctggct tttgtgctgg caaaaccgct gcgtggacca      360
aactgcacgc tgttcgacgt ttacaacgcc acggactatg tgatcccggc gctggagctg      420
atcgacgctc gctgccacaa catcgatccg gaaacccagc gcccgcgtaa agtgttcgac      480
accatttctg ataacgccgc caatgccggg gtgatcctcg gtggtcgtcc cattaagccc      540
gatgagttgg atctacgttg gatctccgcc ctgatgtatc gcaatggcgt gattgaagaa      600
accggcgtcg ccgctggcgt gctgaatcat ccggcaaacg gcgtggcctg gctggcgaac      660
aaactcgccc cctatgacgt acaactggaa gccgggcaaa tcattctcgg cggttcgttc      720
acccgcccgg ttccggcgcg taagggcgac accttccacg tcgattacgg caacatgggc      780
tccattagct gccgctttgt ttaa                                             804
```

```
<210> SEQ ID NO 3
<211> LENGTH: 1593
<212> TYPE: DNA
<213> ORGANISM: Escherichia coli

<400> SEQUENCE: 3
atggaaaaca gttttaaagc ggcgctgaaa gcaggccgtc cgcagattgg attatggctg       60
gggctgagca gcagctacag cgcggagtta ctggccggag caggattcga ctggttgttg      120
atcgacggtg agcacgcacc gaacaacgta caaaccgtgc tcacccagct acaggcgatt      180
gcgccctatc ccagccagcc ggtagtacgt ccgtcgtgga cgatccggt gcaaatcaaa       240 caactgctgg acgtcggcac acaaaccttc tggtgccga tggtacaaaa cgccgacgaa       300
gcccgtgaag cggtacgcgc cacccgttat ccccccgccg gtattcgcgg tgtgggcagt      360
gcgctggctc gcgcctcgcg ctggaatcgc attcctgatt acctgcaaaa agccaacgat      420
caaatgtgcg tgctggtgca gatcgaaacg cgtgaggcaa tgaagaactt accgcagatt      480
ctggacgtgg aaggcgtcga cggcgtgttt atcggcccgg cggatctgag cgccgatatg      540
ggttatgccg gtaatccgca gcacccggaa gtacaggccg ccattgagca ggcgatcgtg      600
cagatccgcg aagcgggcaa agcgccgggg atcctgatcg ccaatgagct actggcaaaa      660
cgctatctgg aactgggcgc gctgtttgtc gccgtcggcg ttgacaccac cctgctcgcc      720
cgcgccgccg aagcgctggc agcacggttt ggcgcgcagg ctacagcgat taagcccggc      780
gtgtattaaa tgttcgacaa acacacccac accctgatcg cccagcgtct ggatcaggca      840
gaaaaacagc gcgaacagat ccgcgcgatc tcgctggatt acccgagat caccatcgaa       900 gacgcttacg cggtgcagcg tgaatgggtt cgactgaaaa tcgccgaagg tcgcacgctg      960
aaaggccaca aaatcggcct gacctcgaaa gcgatgcagg ccagctcgca gatcagcgaa     1020
ccggattacg gtgcactgct ggacgacatg ttcttccacg atggcagcga tatcccgacc     1080
gatcgcttta tcgtgccgcg cattgaagtg gagctggctt ttgtgctggc aaaaccgctg     1140
cgtggaccaa actgcacgct gttcgacgtt tacaacgcca cggactatgt gatcccggcg     1200
ctggagctga tcgacgctcg ctgccacaac atcgatccgg aaacccagcg cccgcgtaaa     1260
gtgttcgaca ccatttctga taacgccgcc aatgccgggg tgatcctcgg tggtcgtccc     1320
attaagcccg atgagttgga tctacgttgg atctccgccc tgatgtatcg caatggcgtg     1380
attgaagaaa ccggcgtcgc cgctggcgtg ctgaatcatc cggcaaacgg cgtggcctgg     1440
ctggcgaaca aactcgcccc ctatgacgta caactggaag ccgggcaaat cattctcggc     1500
ggttcgttca cccgcccggt tccggcgcgt aagggcgaca ccttccacgt cgattacggc     1560
```

```
aacatgggct ccattagctg ccgctttgtt taa                                  1593
```

<210> SEQ ID NO 4
<211> LENGTH: 1098
<212> TYPE: DNA
<213> ORGANISM: Escherichia coli

<400> SEQUENCE: 4

```
atgtcatctg aaaaactgta ttccccactg aaagtgggcg cgatcacggc ggcaaaccgt       60
attttatgg caccgctgac gcgtctgcgc agtattgaac cgggtgacat tcctaccccg      120
ttgatggcgg aatactatcg ccaacgtgcc agtgccggtt tgattattag tgaagccacg      180
caaatttctg cccaggcaaa aggatatgca ggtgcgcctg catccatag tccggagcaa      240
attgccgcat ggaaaaaaat caccgctggc gttcatgctg aaaatggtca tatggccgtg      300
cagctgtggc acaccggacg catttctcac gccagcctgc aacctggcgg tcaggcaccg      360
gtagcgcctt cagcacttag cgcgggaaca cgtacttctc tgcgcgatga aaatggtcag      420
gcgatccgtg ttgaaacatc catgccgcgt gcgcttgaac tggaagagat tccaggtatc      480
gtcaatgatt ccgtcaggc cattgctaac gcgcgtgaag ccggttttga tctggtagag      540
ctccactctg ctcacggtta tttgctgcat cagttccttt ctccttcttc aaaccatcgt      600
accgatcagt acggcggcag cgtggaaaat cgcgcacgtt tggtactgga agtggtcgat      660
gccgggattg aagaatgggg tgccgatcgc attggcattc gcgtttcacc aatcggtact      720
ttccagaaca cagataacgg cccgaatgaa gaagccgatg cactgtatct gattgaacaa      780
ctgggtaaac gcggcattgc ttatctgcat atgtcagaac cagattgggc ggggggtgaa      840
ccgtatactg atgcgttccg cgaaaaagta cgcgcccgtt ccacggtcc gattatcggc      900
gcaggtgcat acacagtaga aaaagctgaa acgctgatcg caaagggtt aattgatgcg      960
gtggcatttg gtcgtgactg gattgcgaac ccggatctgg tcgcccgctt gcagcgcaaa     1020
gctgagctta acccacagcg tgccgaaagt ttctacggtg gcggcgcgga aggctatacc     1080
gattacccga cgttgtaa                                                  1098
```

<210> SEQ ID NO 5
<211> LENGTH: 1644
<212> TYPE: DNA
<213> ORGANISM: Escherichia coli

<400> SEQUENCE: 5

```
atgtatacag taggagatta cctattagac cgattacacg agttaggaat tgaagaaatt       60
tttggagtcc ctggagacta taacttacaa tttttagatc aaattatttc ccgcaaggat      120
atgaaatggg tcgaaatgc taatgaatta atgcttcat atatggctga tggctatgct      180
cgtactaaaa aagctgccgc atttcttaca acctttggag taggtgaatt gagtgcagtt      240
aatggattag caggaagtta cgccgaaaat ttaccagtag tagaaatagt gggatcacct      300
acatcaaaag ttcaaaatga aggaaaattt gttcatcata cgctggctga cggtgatttt      360
aaacacttta tgaaaatgca cgaacctgtt acagcagctc gaactttact gacagcagaa      420
aatgcaaccg ttgaaattga ccgagtactt tctgcactat taaagaaag aaaacctgtc      480
tatatcaact taccagttga tgttgctgct gcaaaagcag agaaacccctc actccctttg      540
aaaaaagaaa actcaacttc aaatacaagt gaccaagaga tcttgaacaa aattcaagaa      600
agcttgaaaa atgccaaaaa accaatcgtg attacaggac atgaaataat tagttttggc      660
```

```
ttagaaaaaa cagtctctca atttatttca aagacaaaac tacctattac gacattaaac      720
tttggaaaaa gttcagttga tgaagctctc ccttcatttt taggaatcta taatggtaaa      780
ctctcagagc ctaatcttaa agaattcgtg gaatcagccg acttcatcct gatgcttgga      840
gttaaactca cagactcttc aacaggagcc ttcactcatc atttaaatga aaataaaatg      900
atttcactga atatagatga aggaaaaata tttaacgaaa gcatccaaaa ttttgatttt      960
gaatccctca tctcctctct cttagaccta agcgaaatag aatacaaagg aaaatatatc     1020 gataaaagc aagaagactt tgttccatca aatgcgcttt tatcacaaga ccgcctatgg     1080
caagcagttg aaaacctaac tcaaagcaat gaaacaatcg ttgctgaaca agggacatca     1140
ttctttggcg cttcatcaat tttcttaaaa ccaaagagtc attttattgg tcaacccta      1200 tggggatcaa ttggatatac attcccagca gcattaggaa gccaaattgc agataaagaa     1260
agcagacacc ttttatttat tggtgatggt tcacttcaac ttacggtgca agaattagga     1320
ttagcaatca gagaaaaaat taatccaatt tgctttatta tcaataatga tggttataca     1380
gtcgaaagag aaattcatgg accaaatcaa agctacaatg atattccaat gtggaattac     1440
tcaaaattac cagaatcatt tggagcaaca gaagaacgag tagtctcgaa aatcgttaga     1500
actgaaaatg aatttgtgtc tgtcatgaaa gaagctcaag cagatccaaa tagaatgtac     1560
tggattgagt taattttggc aaaagaagat gcaccaaaag tactgaaaaa atgggcaaa     1620 ctatttgctg aacaaaataa atca                                            1644

<210> SEQ ID NO 6
<211> LENGTH: 1362
<212> TYPE: DNA
<213> ORGANISM: Escherichia coli

<400> SEQUENCE: 6
atgaaccaac cgcaaagctg ggaagcccgg gccgagacct attcgctcta cggtttcacc       60
gacatgccct cggtccatca gcggggcacg gtcgtcgtga cccatggcga ggggccctat      120
atcgtcgatg tccatggccg ccgctatctg gatgccaatt cgggcctgtg aacatggtc      180 gcgggcttcg accacaaggg cctgatcgag ccgccaaggg cgcaatacga ccgctttccc      240
ggctatcacg cctttttcgg ccgcatgtcc gaccagaccg tgatgctgtc ggaaaagctg      300
gtcgaggtct cgccattcga caacggccgg gtcttctata ccaattccgg ctccgaggcg      360
aacgacacca tggtcaagat gctgtggttc ctgcatgccg ccgagggcaa gccgcaaaag      420
cgcaagatcc tgacgcgctg gaacgcctat acggcgtga ccgcggttc ggcctcgatg       480 accggcaagc cctacaactc ggtcttcggc ctgccgctgc ccggcttcat ccacctgacc      540
tgcccgcatt actggcgcta tggcgaggaa ggcgagaccg aggcgcaatt cgtcgccgc      600 ctggcacgcg agcttgagga taccatcacc gcgagggcg ccgacaccat cgccggcttc      660
ttcgccgagc cggtgatggg cgcgggggg gtgatcccgc cggcgaaggg ttatttccag      720
gccatcctgc cgatcttgcg caagtatgac atcccgatga tctcggacga ggtgatctgc      780
ggcttcgggc gcaccggcaa cacctggggc tgcctgacct acgacttcat gcccgatgcg      840
atcatctcgt ccaagaacct gactgcgggc ttcttcccga tgggcgccgt catcctcggg      900
cccgacctcg ccaagcgggt cgaggccgcg gtcgaggcga tcgaggagtt cccgcacggc      960
ttcaccgcct cgggccatcc ggtcggctgc gccatcgcgc tgaaggccat cgacgtggtg     1020
atgaacgagg gctgggccga gaatgtccgc gcctcgcac cccgcttcga ggcggggctg     1080
aagcgcatcg ccgaccgccc gaacatcggc gaataccgcg gcatcggctt catgtgggcg     1140
```
ctggaggcgg tcaaggacaa gccgaccaag acccccttcg acgccaatct ttcggtcagc    1200
gagcgcatcg ccaatacctg caccgatctg gggctgatct gccggccgct gggccagtcc    1260
atcgtgctgt gcccgccctt catcctgacc gaggcgcaga tggacgagat gttcgaaaag    1320
ctggaaaagg cgctcgacaa ggtctttgcc gaggtggcct ga                       1362

<210> SEQ ID NO 7
<211> LENGTH: 1140
<212> TYPE: DNA
<213> ORGANISM: Escherichia coli

<400> SEQUENCE: 7
atgatctatt ttgataatag tgcgacgacg aagccatatc agaagctctt caatcgtac     60 gtgacggttg ctgggaaata ttttggtaat ccttcttcta ttcattcgct tggaggagag    120
gcagagcgtc tattaacaca atcaagaacg attgcagcgc agcttcttcg tgttaaacct    180
tctgaaatta ttttacatc aggtggaacg aagggaata accttgcgat aaagggata      240 gcgatgagga atcgttcgcg tggcaaacat atcattacaa caaatattga acacgcgtct    300
gtgtttgagg catataagca attagaagaa ctcgggtttg atgtaacata tttaccggtt    360
aacgagcatg gtgttgtgtc ggtagaagat gtgaaacgag cacttcgtga agatacgatt    420
cttgtgtcaa ttattcatgt gaacaacgaa actggagcaa ttcagcccgt tgctgaaatt    480
ggaacgttat tatcgaatca tccgaaaata agattccatg tagatcatgt acaagggata    540
gggaaagtac cgcttgattt atatgcgtct catattgatc tttgctcaat atctggacat    600
aaattccaca gtgtaaaagg aacgggtctt ctttatgtac gcgatggcgt aagattagat    660 ccgatttat caggtggtca acaagagctt aagtatcgtt ctggtacaga aaatttacct     720
ggcattgtag cgatggtgaa agcacttcgt atgacaatgg aacaagtgaa agaaaaggta    780
gctcatttgc aaagtttaca agcagagctt gttcgtttct ttaaagagat ggaagatgta    840
acgattaaca cgtcgcttgc atatgcagca ccgcacattt taaatgtatc atttgttggt    900
ttaaaaccag aagtagtcgt tcatgcttta gaagaacacg tgtatatgt gtcaacgaaa     960 tctgcttgtt cttcaaaagc aaatgaagtg agcagagtgt tagtgtcaat gggagtgccg    1020
catgcagcag ctgcaagcgc tattcgtatt agtttggcac cagaaaacac aatggaagaa    1080
gtaaaacaat tgaaggtat tgtaaaagag acgatgccaa aattatatga agtgatgagg     1140

<210> SEQ ID NO 8
<211> LENGTH: 262
<212> TYPE: PRT
<213> ORGANISM: Escherichia coli

<400> SEQUENCE: 8

Met Glu Asn Ser Phe Lys Ala Ala Leu Lys Ala Gly Arg Pro Gln Ile
1               5                   10                  15

Gly Leu Trp Leu Gly Leu Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
    50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln

```
                    85                  90                  95
Asn Ala Asp Glu Ala Arg Glu Ala Val Arg Ala Thr Arg Tyr Pro Pro
            100                 105                 110

Ala Gly Ile Arg Gly Val Gly Ser Ala Leu Arg Ala Ser Arg Trp
            115                 120                 125

Asn Arg Ile Pro Asp Tyr Leu Gln Lys Ala Asn Asp Gln Met Cys Val
            130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
                180                 185                 190

Ala Ala Ile Glu Gln Ala Ile Val Gln Ile Arg Glu Ala Gly Lys Ala
                195                 200                 205

Pro Gly Ile Leu Ile Ala Asn Glu Leu Leu Ala Lys Arg Tyr Leu Glu
            210                 215                 220

Leu Gly Ala Leu Phe Val Ala Val Gly Val Asp Thr Thr Leu Leu Ala
225                 230                 235                 240

Arg Ala Glu Ala Leu Ala Ala Arg Phe Gly Ala Gln Ala Thr Ala
                245                 250                 255

Ile Lys Pro Gly Val Tyr
            260

<210> SEQ ID NO 9
<211> LENGTH: 267
<212> TYPE: PRT
<213> ORGANISM: Escherichia coli

<400> SEQUENCE: 9

Met Phe Asp Lys His Thr His Thr Leu Ile Ala Gln Arg Leu Asp Gln
1               5                   10                  15

Ala Glu Lys Gln Arg Glu Gln Ile Arg Ala Ile Ser Leu Asp Tyr Pro
                20                  25                  30

Glu Ile Thr Ile Glu Asp Ala Tyr Ala Val Gln Arg Glu Trp Val Arg
            35                  40                  45

Leu Lys Ile Ala Glu Gly Arg Thr Leu Lys Gly His Lys Ile Gly Leu
        50                  55                  60

Thr Ser Lys Ala Met Gln Ala Ser Ser Gln Ile Ser Glu Pro Asp Tyr
65                  70                  75                  80

Gly Ala Leu Leu Asp Asp Met Phe Phe His Asp Gly Ser Asp Ile Pro
                85                  90                  95

Thr Asp Arg Phe Ile Val Pro Arg Ile Glu Val Glu Leu Ala Phe Val
            100                 105                 110

Leu Ala Lys Pro Leu Arg Gly Pro Asn Cys Thr Leu Phe Asp Val Tyr
            115                 120                 125

Asn Ala Thr Asp Tyr Val Ile Pro Ala Leu Glu Leu Ile Asp Ala Arg
            130                 135                 140

Cys His Asn Ile Asp Pro Glu Thr Gln Arg Pro Arg Lys Val Phe Asp
145                 150                 155                 160

Thr Ile Ser Asp Asn Ala Ala Asn Ala Gly Val Ile Leu Gly Gly Arg
                165                 170                 175

Pro Ile Lys Pro Asp Glu Leu Asp Leu Arg Trp Ile Ser Ala Leu Met
            180                 185                 190
```

```
Tyr Arg Asn Gly Val Ile Glu Glu Thr Gly Val Ala Ala Gly Val Leu
            195                 200                 205

Asn His Pro Ala Asn Gly Val Ala Trp Leu Ala Asn Lys Leu Ala Pro
        210                 215                 220

Tyr Asp Val Gln Leu Glu Ala Gly Gln Ile Ile Leu Gly Gly Ser Phe
225                 230                 235                 240

Thr Arg Pro Val Pro Ala Arg Lys Gly Asp Thr Phe His Val Asp Tyr
                245                 250                 255

Gly Asn Met Gly Ser Ile Ser Cys Arg Phe Val
            260                 265

<210> SEQ ID NO 10
<211> LENGTH: 529
<212> TYPE: PRT
<213> ORGANISM: Escherichia coli

<400> SEQUENCE: 10

Met Glu Asn Ser Phe Lys Ala Ala Leu Lys Ala Gly Arg Pro Gln Ile
1               5                   10                  15

Gly Leu Trp Leu Gly Leu Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
    50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln
                85                  90                  95

Asn Ala Asp Glu Ala Arg Glu Ala Val Arg Ala Thr Arg Tyr Pro Pro
            100                 105                 110

Ala Gly Ile Arg Gly Val Gly Ser Ala Leu Ala Arg Ala Ser Arg Trp
        115                 120                 125

Asn Arg Ile Pro Asp Tyr Leu Gln Lys Ala Asn Asp Gln Met Cys Val
130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
            180                 185                 190

Ala Ala Ile Glu Gln Ala Ile Val Gln Ile Arg Glu Ala Gly Lys Ala
        195                 200                 205

Pro Gly Ile Leu Ile Ala Asn Glu Leu Leu Ala Lys Arg Tyr Leu Glu
    210                 215                 220

Leu Gly Ala Leu Phe Val Ala Val Gly Val Asp Thr Thr Leu Leu Ala
225                 230                 235                 240

Arg Ala Ala Glu Ala Leu Ala Ala Arg Phe Gly Ala Gln Ala Thr Ala
                245                 250                 255

Ile Lys Pro Gly Val Tyr Met Phe Asp Lys His Thr His Thr Leu Ile
            260                 265                 270

Ala Gln Arg Leu Asp Gln Ala Glu Lys Gln Arg Glu Gln Ile Arg Ala
        275                 280                 285

Ile Ser Leu Asp Tyr Pro Glu Ile Thr Ile Glu Asp Ala Tyr Ala Val
    290                 295                 300
```

Gln Arg Glu Trp Val Arg Leu Lys Ile Ala Glu Gly Arg Thr Leu Lys
305                 310                 315                 320

Gly His Lys Ile Gly Leu Thr Ser Lys Ala Met Gln Ala Ser Ser Gln
                325                 330                 335

Ile Ser Glu Pro Asp Tyr Gly Ala Leu Leu Asp Asp Met Phe Phe His
            340                 345                 350

Asp Gly Ser Asp Ile Pro Thr Asp Arg Phe Ile Val Pro Arg Ile Glu
        355                 360                 365

Val Glu Leu Ala Phe Val Leu Ala Lys Pro Leu Arg Gly Pro Asn Cys
    370                 375                 380

Thr Leu Phe Asp Val Tyr Asn Ala Thr Asp Tyr Val Ile Pro Ala Leu
385                 390                 395                 400

Glu Leu Ile Asp Ala Arg Cys His Asn Ile Asp Pro Glu Thr Gln Arg
                405                 410                 415

Pro Arg Lys Val Phe Asp Thr Ile Ser Asp Asn Ala Ala Asn Ala Gly
            420                 425                 430

Val Ile Leu Gly Gly Arg Pro Ile Lys Pro Asp Glu Leu Asp Leu Arg
        435                 440                 445

Trp Ile Ser Ala Leu Met Tyr Arg Asn Gly Val Ile Glu Glu Thr Gly
    450                 455                 460

Val Ala Ala Gly Val Leu Asn His Pro Ala Asn Gly Val Ala Trp Leu
465                 470                 475                 480

Ala Asn Lys Leu Ala Pro Tyr Asp Val Gln Leu Glu Ala Gly Gln Ile
                485                 490                 495

Ile Leu Gly Gly Ser Phe Thr Arg Pro Val Pro Ala Arg Lys Gly Asp
            500                 505                 510

Thr Phe His Val Asp Tyr Gly Asn Met Gly Ser Ile Ser Cys Arg Phe
        515                 520                 525

Val

<210> SEQ ID NO 11
<211> LENGTH: 365
<212> TYPE: PRT
<213> ORGANISM: Escherichia coli

<400> SEQUENCE: 11

Met Ser Ser Glu Lys Leu Tyr Ser Pro Leu Lys Val Gly Ala Ile Thr
1               5                   10                  15

Ala Ala Asn Arg Ile Phe Met Ala Pro Leu Thr Arg Leu Arg Ser Ile
                20                  25                  30

Glu Pro Gly Asp Ile Pro Thr Pro Leu Met Ala Glu Tyr Tyr Arg Gln
            35                  40                  45

Arg Ala Ser Ala Gly Leu Ile Ile Ser Glu Ala Thr Gln Ile Ser Ala
        50                  55                  60

Gln Ala Lys Gly Tyr Ala Gly Ala Pro Gly Ile His Ser Pro Glu Gln
65                  70                  75                  80

Ile Ala Ala Trp Lys Lys Ile Thr Ala Gly Val His Ala Glu Asn Gly
                85                  90                  95

His Met Ala Val Gln Leu Trp His Thr Gly Arg Ile Ser His Ala Ser
            100                 105                 110

Leu Gln Pro Gly Gly Gln Ala Pro Val Ala Pro Ser Ala Leu Ser Ala
        115                 120                 125

Gly Thr Arg Thr Ser Leu Arg Asp Glu Asn Gly Gln Ala Ile Arg Val
    130                 135                 140

Glu Thr Ser Met Pro Arg Ala Leu Glu Leu Glu Ile Pro Gly Ile
145                 150                 155                 160

Val Asn Asp Phe Arg Gln Ala Ile Ala Asn Ala Arg Glu Ala Gly Phe
            165                 170                 175

Asp Leu Val Glu Leu His Ser Ala His Gly Tyr Leu Leu His Gln Phe
        180                 185                 190

Leu Ser Pro Ser Ser Asn His Arg Thr Asp Gln Tyr Gly Gly Ser Val
            195                 200                 205

Glu Asn Arg Ala Arg Leu Val Leu Glu Val Val Asp Ala Gly Ile Glu
        210                 215                 220

Glu Trp Gly Ala Asp Arg Ile Gly Ile Arg Val Ser Pro Ile Gly Thr
225                 230                 235                 240

Phe Gln Asn Thr Asp Asn Gly Pro Asn Glu Glu Ala Asp Ala Leu Tyr
            245                 250                 255

Leu Ile Glu Gln Leu Gly Lys Arg Gly Ile Ala Tyr Leu His Met Ser
        260                 265                 270

Glu Pro Asp Trp Ala Gly Gly Glu Pro Tyr Thr Asp Ala Phe Arg Glu
            275                 280                 285

Lys Val Arg Ala Arg Phe His Gly Pro Ile Ile Gly Ala Gly Ala Tyr
        290                 295                 300

Thr Val Glu Lys Ala Glu Thr Leu Ile Gly Lys Gly Leu Ile Asp Ala
305                 310                 315                 320

Val Ala Phe Gly Arg Asp Trp Ile Ala Asn Pro Asp Leu Val Ala Arg
            325                 330                 335

Leu Gln Arg Lys Ala Glu Leu Asn Pro Gln Arg Ala Glu Ser Phe Tyr
        340                 345                 350

Gly Gly Gly Ala Glu Gly Tyr Thr Asp Tyr Pro Thr Leu
            355                 360                 365

<210> SEQ ID NO 12
<211> LENGTH: 548
<212> TYPE: PRT
<213> ORGANISM: Escherichia coli

<400> SEQUENCE: 12

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
            85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val

```
              145                 150                 155                 160
Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525

Glu Asp Ala Pro Lys Val Leu Lys Lys Met Gly Lys Leu Phe Ala Glu
                530                 535                 540

Gln Asn Lys Ser
545

<210> SEQ ID NO 13
```

<211> LENGTH: 453
<212> TYPE: PRT
<213> ORGANISM: Escherichia coli

<400> SEQUENCE: 13

Met Asn Gln Pro Gln Ser Trp Glu Ala Arg Ala Glu Thr Tyr Ser Leu
1               5                   10                  15

Tyr Gly Phe Thr Asp Met Pro Ser Val His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Glu Ala Ala Lys Ala Gln Tyr Asp Arg Phe Pro
65                  70                  75                  80

Gly Tyr His Ala Phe Gly Arg Met Ser Asp Gln Thr Val Met Leu
                85                  90                  95

Ser Glu Lys Leu Val Glu Val Ser Pro Phe Asp Asn Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Ile His Leu Thr Cys Pro His Tyr Trp Arg Tyr Gly Glu Glu Gly Glu
            180                 185                 190

Thr Glu Ala Gln Phe Val Ala Arg Leu Ala Arg Glu Leu Glu Asp Thr
        195                 200                 205

Ile Thr Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Met Ile Ser Asp
                245                 250                 255

Glu Val Ile Cys Gly Phe Gly Arg Thr Gly Asn Thr Trp Gly Cys Leu
            260                 265                 270

Thr Tyr Asp Phe Met Pro Asp Ala Ile Ile Ser Ser Lys Asn Leu Thr
        275                 280                 285

Ala Gly Phe Phe Pro Met Gly Ala Val Ile Leu Gly Pro Asp Leu Ala
    290                 295                 300

Lys Arg Val Glu Ala Val Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Ala Gly Leu Lys Arg Ile Ala Asp Arg Pro Asn
        355                 360                 365

Ile Gly Glu Tyr Arg Gly Ile Gly Phe Met Trp Ala Leu Glu Ala Val
    370                 375                 380

Lys Asp Lys Pro Thr Lys Thr Pro Phe Asp Ala Asn Leu Ser Val Ser

```
385                 390                 395                 400
Glu Arg Ile Ala Asn Thr Cys Thr Asp Leu Gly Leu Ile Cys Arg Pro
                405                 410                 415

Leu Gly Gln Ser Ile Val Leu Cys Pro Pro Phe Ile Leu Thr Glu Ala
            420                 425                 430

Gln Met Asp Glu Met Phe Glu Lys Glu Lys Ala Leu Asp Lys Val
        435                 440                 445

Phe Ala Glu Val Ala
        450

<210> SEQ ID NO 14
<211> LENGTH: 380
<212> TYPE: PRT
<213> ORGANISM: Escherichia coli

<400> SEQUENCE: 14

Met Ile Tyr Phe Asp Asn Ser Ala Thr Thr Lys Pro Tyr Pro Glu Ala
1               5                   10                  15

Leu Gln Ser Tyr Val Thr Val Ala Gly Lys Tyr Phe Gly Asn Pro Ser
            20                  25                  30

Ser Ile His Ser Leu Gly Gly Glu Ala Glu Arg Leu Leu Thr Gln Ser
        35                  40                  45

Arg Thr Ile Ala Ala Gln Leu Leu Arg Val Lys Pro Ser Glu Ile Ile
    50                  55                  60

Phe Thr Ser Gly Gly Thr Glu Gly Asn Asn Leu Ala Ile Lys Gly Ile
65                  70                  75                  80

Ala Met Arg Asn Arg Ser Arg Gly Lys His Ile Ile Thr Thr Asn Ile
                85                  90                  95

Glu His Ala Ser Val Phe Glu Ala Tyr Lys Gln Leu Glu Glu Leu Gly
            100                 105                 110

Phe Asp Val Thr Tyr Leu Pro Val Asn Glu His Gly Val Val Ser Val
        115                 120                 125

Glu Asp Val Lys Arg Ala Leu Arg Glu Asp Thr Ile Leu Val Ser Ile
    130                 135                 140

Ile His Val Asn Asn Glu Thr Gly Ala Ile Gln Pro Val Ala Glu Ile
145                 150                 155                 160

Gly Thr Leu Leu Ser Asn His Pro Lys Ile Arg Phe His Val Asp His
                165                 170                 175

Val Gln Gly Ile Gly Lys Val Pro Leu Asp Leu Tyr Ala Ser His Ile
            180                 185                 190

Asp Leu Cys Ser Ile Ser Gly His Lys Phe His Ser Val Lys Gly Thr
        195                 200                 205

Gly Leu Leu Tyr Val Arg Asp Gly Val Arg Leu Asp Pro Ile Leu Ser
    210                 215                 220

Gly Gly Gln Gln Glu Leu Lys Tyr Arg Ser Gly Thr Glu Asn Leu Pro
225                 230                 235                 240

Gly Ile Val Ala Met Val Lys Ala Leu Arg Met Thr Met Glu Gln Val
                245                 250                 255

Lys Glu Lys Val Ala His Leu Gln Ser Leu Gln Ala Glu Leu Val Arg
            260                 265                 270

Phe Phe Lys Glu Met Glu Asp Val Thr Ile Asn Thr Ser Leu Ala Tyr
        275                 280                 285

Ala Ala Pro His Ile Leu Asn Val Ser Phe Val Gly Leu Lys Pro Glu
    290                 295                 300
```

Val Val Val His Ala Leu Glu Glu His Gly Val Tyr Val Ser Thr Lys
305                 310                 315                 320

Ser Ala Cys Ser Ser Lys Ala Asn Glu Val Ser Arg Val Leu Val Ser
            325                 330                 335

Met Gly Val Pro His Ala Ala Ala Ser Ala Ile Arg Ile Ser Leu
        340                 345                 350

Ala Pro Glu Asn Thr Met Glu Glu Val Lys Gln Phe Glu Gly Ile Val
        355                 360                 365

Lys Glu Thr Met Pro Lys Leu Tyr Glu Val Met Arg
    370                 375                 380

<210> SEQ ID NO 15
<211> LENGTH: 42
<212> TYPE: DNA
<213> ORGANISM: Artificial Sequence
<220> FEATURE:
<223> OTHER INFORMATION: hpaI_F primer

<400> SEQUENCE: 15
cgcgcggcag ccatatgatg gaaaacagtt ttaaagcggc gc                42

<210> SEQ ID NO 16
<211> LENGTH: 38
<212> TYPE: DNA
<213> ORGANISM: Artificial Sequence
<220> FEATURE:
<223> OTHER INFORMATION: hpaI_R primer

<400> SEQUENCE: 16
ggtggtggtg ctcgagatac acgccgggct taatcgct                    38

<210> SEQ ID NO 17
<211> LENGTH: 41
<212> TYPE: DNA
<213> ORGANISM: Artificial Sequence
<220> FEATURE:
<223> OTHER INFORMATION: hpaH_F primer

<400> SEQUENCE: 17
cgcgcggcag ccatatgatg ttcgacaaac acccacac c                  41

<210> SEQ ID NO 18
<211> LENGTH: 39
<212> TYPE: DNA
<213> ORGANISM: Artificial Sequence
<220> FEATURE:
<223> OTHER INFORMATION: hpaH_R primer

<400> SEQUENCE: 18
ggtggtggtg ctcgagaaca aagcggcagc taatggagc                   39

<210> SEQ ID NO 19
<211> LENGTH: 43
<212> TYPE: DNA
<213> ORGANISM: Artificial Sequence
<220> FEATURE:
<223> OTHER INFORMATION: nemA_F primer

<400> SEQUENCE: 19
cgcgcggcag ccatatgatg tcatctgaaa aactgtattc ccc              43

<210> SEQ ID NO 20
<211> LENGTH: 39
<212> TYPE: DNA

```
<213> ORGANISM: Artificial Sequence
<220> FEATURE:
<223> OTHER INFORMATION: nemA_R primer

<400> SEQUENCE: 20
ggtggtggtg ctcgagcaac gtcgggtaat cggtatagc                    39

<210> SEQ ID NO 21
<211> LENGTH: 43
<212> TYPE: DNA
<213> ORGANISM: Artificial Sequence
<220> FEATURE:
<223> OTHER INFORMATION: KIVD_F primer

<400> SEQUENCE: 21
cgcgcggcag ccatatgatg tatacagtag gagattacct att               43

<210> SEQ ID NO 22
<211> LENGTH: 43
<212> TYPE: DNA
<213> ORGANISM: Artificial Sequence
<220> FEATURE:
<223> OTHER INFORMATION: KIVD_R primer

<400> SEQUENCE: 22
ggtggtggtg ctcgagtgat ttattttgtt cagcaaatag ttt               43

<210> SEQ ID NO 23
<211> LENGTH: 41
<212> TYPE: DNA
<213> ORGANISM: Artificial Sequence
<220> FEATURE:
<223> OTHER INFORMATION: BcAT_F primer

<400> SEQUENCE: 23
cgcgcggcag ccatatgatg atctattttg ataatagtgc g                 41

<210> SEQ ID NO 24
<211> LENGTH: 40
<212> TYPE: DNA
<213> ORGANISM: Artificial Sequence
<220> FEATURE:
<223> OTHER INFORMATION: BcAT_R primer

<400> SEQUENCE: 24
ggtggtggtg ctcgagcctc atcacttcat ataattttgg                   40

<210> SEQ ID NO 25
<211> LENGTH: 35
<212> TYPE: DNA
<213> ORGANISM: Artificial Sequence
<220> FEATURE:
<223> OTHER INFORMATION: PdAT_F primer

<400> SEQUENCE: 25
cgcgcggcag ccatatgatg aaccaaccgc aaagc                        35

<210> SEQ ID NO 26
<211> LENGTH: 31
<212> TYPE: DNA
<213> ORGANISM: Artificial Sequence
<220> FEATURE:
<223> OTHER INFORMATION: PdAT_R primer

<400> SEQUENCE: 26
ggtggtggtg ctcgagggcc acctcggcaa a                            31
```

<210> SEQ ID NO 27
<211> LENGTH: 41
<212> TYPE: DNA
<213> ORGANISM: Artificial Sequence
<220> FEATURE:
<223> OTHER INFORMATION: pACYC hpaIH_F primer

<400> SEQUENCE: 27
cgatactatg actgataata cgactcacta tagggaatt g                41

<210> SEQ ID NO 28
<211> LENGTH: 35
<212> TYPE: DNA
<213> ORGANISM: Artificial Sequence
<220> FEATURE:
<223> OTHER INFORMATION: pACYC hpaIH_R primer

<400> SEQUENCE: 28
catggcgttg actctcaaaa aaccccctcaa gaccc                     35

<210> SEQ ID NO 29
<211> LENGTH: 41
<212> TYPE: DNA
<213> ORGANISM: Artificial Sequence
<220> FEATURE:
<223> OTHER INFORMATION: pACYC nemA_F primer

<400> SEQUENCE: 29
cccgtcctgt ggatgtaata cgactcacta tagggaatt g                41

<210> SEQ ID NO 30
<211> LENGTH: 35
<212> TYPE: DNA
<213> ORGANISM: Artificial Sequence
<220> FEATURE:
<223> OTHER INFORMATION: pACYC nemA_R primer

<400> SEQUENCE: 30
ccggcgtaga ggatccaaaa aaccccctcaa gaccc                     35

<210> SEQ ID NO 31
<211> LENGTH: 41
<212> TYPE: DNA
<213> ORGANISM: Artificial Sequence
<220> FEATURE:
<223> OTHER INFORMATION: pACYC KIVD_F primer

<400> SEQUENCE: 31
aagggagagc gtcgataata cgactcacta tagggaatt g                41

<210> SEQ ID NO 32
<211> LENGTH: 35
<212> TYPE: DNA
<213> ORGANISM: Artificial Sequence
<220> FEATURE:
<223> OTHER INFORMATION: pACYC KIVD_R primer

<400> SEQUENCE: 32
aagggcatcg gtcgacaaaa aaccccctcaa gaccc                     35

<210> SEQ ID NO 33
<211> LENGTH: 41
<212> TYPE: DNA
<213> ORGANISM: Artificial Sequence
<220> FEATURE:

```
<223> OTHER INFORMATION: pACYC BcAT_F primer

<400> SEQUENCE: 33
ccatctcctt gcatgtaata cgactcacta taggggaatt g                          41

<210> SEQ ID NO 34
<211> LENGTH: 35
<212> TYPE: DNA
<213> ORGANISM: Artificial Sequence
<220> FEATURE:
<223> OTHER INFORMATION: pACYC BcAT_R primer

<400> SEQUENCE: 34
aaggaatggt gcatgcaaaa aacccctcaa gaccc                                 35

<210> SEQ ID NO 35
<211> LENGTH: 41
<212> TYPE: DNA
<213> ORGANISM: Artificial Sequence
<220> FEATURE:
<223> OTHER INFORMATION: pACYC PdAT_F primer

<400> SEQUENCE: 35
tatcatcgat aagcttaata cgactcacta taggggaatt g                          41

<210> SEQ ID NO 36
<211> LENGTH: 35
<212> TYPE: DNA
<213> ORGANISM: Artificial Sequence
<220> FEATURE:
<223> OTHER INFORMATION: pACYC PdAT_R primer

<400> SEQUENCE: 36
taccgcatta aagctcaaaa aacccctcaa gaccc                                 35
```

BIOLOGICAL SYNTHESIS OF 6-AMINOCAPROIC ACID AND TRANSGENIC MICROORGANISM THEREFOR

A computer readable text file, entitled "SequenceListing.txt," created on or about Mar. 11, 2016 with a file size of about 40 kb contains the sequence listing for this application and is hereby incorporated by reference in its entirety.

TECHNICAL FIELD

The present invention relates to a recombinant microorganism for the biological synthesis of 6-aminocaproic acid in the microorganism so as to synthesize caprolactam.

BACKGROUND ART

Caprolactam, which is an organic compound, is a lactam of 6-aminohexanoic acid (ε-aminohexanoic acid, 6-aminocaproic acid). Unlike other compounds, caprolactam can be considered as a cyclic amide of caproic acid. One use of caprolactam is as a monomer in the production of nylon 6. Base materials that are most widely used in the production of caprolactam are aromatic compounds such as benzene, phenol, toluene, etc. Caprolactam is ultimately synthesized via the Beckmann rearrangement using sulfur catalysts by preparing oxime compounds via oximation, which drives a reaction of cyclohexanone with hydroxylamine obtained from the base materials of the aromatic compounds. When caprolactam is synthesized via such process, it is difficult to avoid formation of ammonium sulfate as a byproduct. In the production of caprolactam, the yield of caprolactam decreases as more ammonium sulfate is produced, and therefore, caprolactam can be obtained in high yield only if the formation of ammonium sulfate is suppressed.

Recent development trends for production techniques of caprolactam are divided into developing processes for reducing or eliminating the formation of ammonium sulfate or developing alternative base materials therefor. One example of the former development includes a caprolactam production facility recently developed by Sumitomo Chemical, Japan. This involves the Beckmann rearrangement in a gas phase using fluid bed gas-phase zeolite-catalysts and an ammoximation reaction using hydrogen peroxide catalysts (Enichem). Also, the base materials developed as alternatives for caprolactam include hexamethylene diamine (HMDA) and tetramethylene diamine (TMDA). HMDA can be produced from adiponitrile, propylene, and acrylonitrile. However, the process for HMDA production using adiponitrile can only be used by BASF, Solutia, Butachimie, and DuPont. Adiponitrile is produced by reacting butadiene with hydrogen cyanide. Butadiene may be used as a base material for adipic acid, which is a base material for nylon 4 and nylon 6. Most of the intermediates used in the production of nylon have their origins in butadiene, and such tendency is increasingly spreading.

As such, much more attention has been drawn to the production of these chemicals and materials from renewable non-food biomass via biorefinery as concerns about environmental problems and the availability of fossil resources increase. With the development of the biorefinery processes, microorganisms have been used as core biocatalysts capable of successfully producing chemicals, plastics, and fuels from renewable resources. However, non-manipulated natural microorganisms are not suitable for efficiently producing target products at the industrial level due to their reduced metabolism. Therefore, techniques that improve the metabolism of microorganisms have been actively studied to efficiently produce target products. Many studies are being conducted to solve the optimization of these microorganisms via systems metabolic engineering at the system level.

Accordingly, the present inventors have constructed a transformed microorganism capable of biosynthesizing 6-aminocaproic acid in the microorganism by expressing genes of enzymes used in the biosynthetic pathway of 6-aminocaproic acid, which is a precursor of caprolactam, to produce caprolactam.

DISCLOSURE

Technical Problem

An object of the present invention is to provide a method for producing 6-aminocaproic acid.

Another object of the present invention is to provide an expression vector for biosynthesis of 6-aminocaproic acid comprising HpaI (4-hydroxy-2-oxoheptane-1,7-dioate aldolase)-HpaH (2-oxohept-3-ene-1,7-dioate dehydratase) gene, nemA (N-ethylmaleimide reductase) gene, KIVD (alpha-ketoisovalerate decarboxylase) gene; and at least one of PdAT (beta-alanine-pyruvate transaminase) and BcAT (adenosylmethionine-8-amino-7-oxononanoate aminotransferase).

A further object of the present invention is to provide a transformant transformed with the expression vector above.

Yet another object of the present invention is to provide a method for producing caprolactam further comprising converting 6-aminocaproic acid produced by the method for producing 6-aminocaproic acid to caprolactam.

Technical Solution

In order to accomplish the above objects, the present invention provides a method for producing 6-aminocaproic acid.

Also, the present invention provides an expression vector for the biosynthesis of 6-aminocaproic acid comprising HpaI (4-hydroxy-2-oxoheptane-1,7-dioate aldolase)-HpaH (2-oxohept-3-ene-1,7-dioate dehydratase) gene, nemA (N-ethylmaleimide reductase) gene, KIVD (alpha-ketoisovalerate decarboxylase) gene; and at least one of PdAT (beta-alanine-pyruvate transaminase) and BcAT (adenosylmethionine-8-amino-7-oxononanoate aminotransferase).

Further, the present invention provides a transformant transformed with the expression vector above.

Furthermore, the present invention provides a method for producing caprolactam further comprising converting 6-aminocaproic acid produced by the method for producing 6-aminocaproic acid to caprolactam.

Advantageous Effects

A microorganism transformed into an expression vector comprising HpaI (4-hydroxy-2-oxoheptane-1,7-dioate aldolase)-HpaH (2-oxohept-3-ene-1,7-dioate dehydratase) gene, nemA (N-ethylmaleimide reductase) gene, and KIVD (alpha-ketoisovalerate decarboxylase) gene; and at least one of PdAT (beta-alanine-pyruvate transaminase) and BcAT (adenosylmethionine-8-amino-7-oxononanoate aminotransferase) genes encoding enzymes used in the biosynthetic pathway of 6-aminocaproic acid can efficiently biosynthesize 6-aminocaproic acid, and thus, it can be used in the synthesis of caprolactam.

BEST MODE

Figure 1:
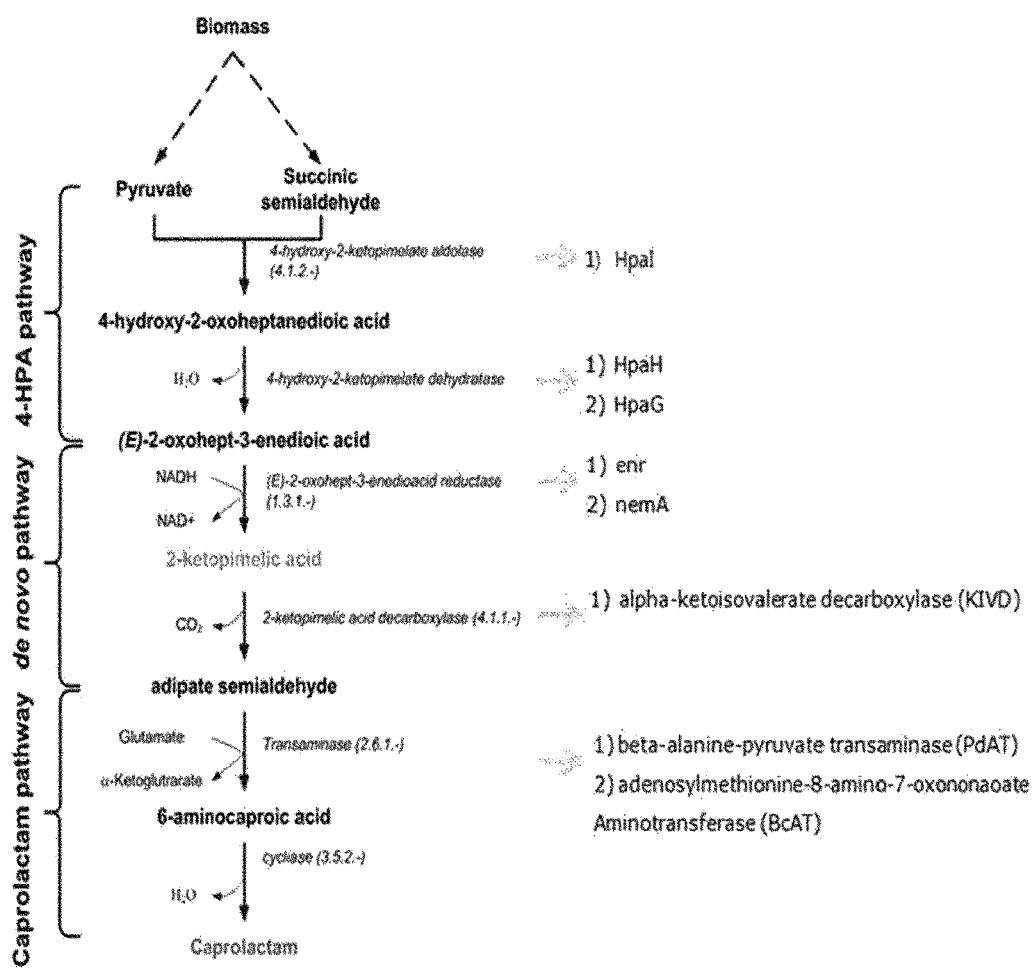
FIG. 1 is a schematic diagram showing enzymes and genes encoding the enzymes used in the biosynthetic pathway of 6-aminocaproic acid.

Hereinbelow, the present invention is described in detail.

As used herein, the terms "polynucleotide", "oligonucleotide", and "nucleic acid" have identical meaning, and represent nucleotide polymers having any length. Such terms also include "oligonucleotide derivatives" or "polynucleotide derivatives". "Oligonucleotide derivatives" or "polynucleotide derivatives" may include nucleotide derivatives or may represent oligonucleotides or polynucleotides having a general system or a different system between nucleotides, and they are used interchangeably.

As used herein, the term "polynucleotide" is used interchangeably with nucleic acid, oligonucleotide, and polynucleotide, and may include cDNA, mRNA, genome DNA, etc. The polynucleotide used herein is included by the term "genes". A polynucleotide encoding gene sequences may include "splicing variants". Similarly, specific proteins encoded by nucleic acid may include proteins encoded by splicing variants encoded thereby. As the name indicates, the term "splicing variants" represents a product of alternative splicing variants. The first nucleic acid transcriptome after transcription is spliced by encoding other polypeptides which are identical to a product of distinct nucleic acid variants. They may include exon-selective splicing even if a mechanism of splicing variant formation is different. Other polypeptides derived from identical nucleic acids by incorrect transcription may include such definitions. Products (including splicing products in the form of a recombinant) of a splicing reaction may be included in the definitions.

As used herein, the term "expression" of a gene product, such as a polynucleotide and a polypeptide, may represent transformation of a gene into another form under the influence of predetermined action in vivo. Preferably, the term "expression" represents transcription of genes, polynucleotides, etc. and translation into polypeptides. In an embodiment of the present invention, genes are transcribed into mRNA. More preferably, the polypeptides undergo post-translation modifications. Accordingly, a "reduction" in "expression" of genes, polynucleotides, and polypeptides used herein represents a significant reduction when an agent of the present invention is applied, compared to when no agent is applied. Preferably, the reduction in expression may include a reduction in expression level of polypeptides. More specifically, the reduction in expression level represents a reduction in expression by at least 10%, preferably by at least 20%, more preferably by at least 30%, still more preferably by at least 40%, still more preferably by at least 50%, still more preferably by at least 75%, still more preferably by at least 90%, and most preferably by at least 100%, when compared before and after applying the agent. An "increase" in "expression" of genes, polynucleotides, and polypeptides used herein represents a significant increase when an agent of the present invention is applied, compared to when no agent is applied. Preferably, the increase in expression may include an increase in an expression level of polypeptides. More specifically, the increase in the expression level represents an increase by at least 10%, preferably by at least 20%, more preferably by at least 30%, still more preferably by at least 40%, still more preferably by at least 50%, still more preferably by at least 75%, still more preferably by at least 90%, still more preferably by at least 100%, and most preferably by at least 200%, when compared before and after applying the agent, or an occurrence of expression before the agent is applied in which no expression occurs.

The present invention provides a method for preparing 6-aminocaproic acid comprising: preparing an expression vector comprising HpaI (4-hydroxy-2-oxoheptane-1,7-dioate aldolase)-HpaH (2-oxohept-3-ene-1,7-dioate dehydratase) gene, nemA (N-ethylmaleimide reductase) gene, and KIVD (alpha-ketoisovalerate decarboxylase) gene; and at least one of PdAT (beta-alanine-pyruvate transaminase) and BcAT (adenosylmethionine-8-amino-7-oxononanoate aminotransferase) (step 1); and transforming the expression vector of step 1 into a microorganism (step 2).

The HpaI-HpaH gene preferably includes a polynucleotide represented by SEQ ID NO: 3 encoding aldolase-dehydratase, which converts pyruvate and/or succinic semialdehyde (SSA) into 2-oxohept-3-enedioic acid, but is not limited thereto.

The nemA gene preferably includes a polynucleotide represented by SEQ ID NO: 4 encoding reductase, which converts 2-oxohept-3-enedioic acid into 2-ketopimelic acid, but is not limited thereto.

The KIVD (alpha-ketoisovalerate decarboxylase) gene preferably includes a polynucleotide represented by SEQ ID NO: 5 encoding decarboxylase, which converts 2-ketopimelic acid into adipate semialdehyde, but is not limited thereto.

The PdAT (beta-alanine-pyruvate transaminase) gene preferably includes a polynucleotide represented by SEQ ID NO: 6 encoding transaminase, which converts adipate semialdehyde into 6-aminocaproic acid, but is not limited thereto.

The BcAT (adenosylmethionine-8-amino-7-oxononanoate aminotransferase) gene preferably includes a polynucleotide represented by SEQ ID NO: 7 encoding transaminase, which converts adipate semialdehyde into 6-aminocaproic acid, but is not limited thereto.

The expression vector of step 1 may further include nucleic acid sequences encoding GST, MBP, NusA, thioredoxin, ubiquitin, FLAG, BAP, 6HIS, STREP, CBP, CBD, or S-tag affinity tag, but is not limited thereto.

The expression vector of step 1 may further include nucleic acid sequences encoding kex2p in yeasts, purine in mammals, Factor Xa, enterokinase, subtilisin, tobacco etch virus protease, thrombin, or ubiquitin hydrolase, but is not limited thereto.

The microorganisms of step 2 may preferably be a bacterium, yeast, or fungus.

The method may further include producing and secreting 6-aminocaproic acid by culturing the transformed microorganism of step 2 in a fed-batch fermentation, but is not limited thereto.

The method may further include purifying the protein secreted above, but is not limited thereto.

The polynucleotides of the present invention may include amino acid sequences having a homology to each of the above-listed amino acid sequences of more than 70%, more preferably more than 80%, even more preferably more than 90%, and most preferably more than 95%. The "sequence homology percentage" may be confirmed through comparison between two sequences having an optimal arrangement and a region to be compared, and some parts of polynucleotide sequence in the region to be compared may include addition or deletion (i.e., gaps), compared to reference sequences (where addition or deletion is not included) for the optimal arrangement of the two sequences.

Also, the present invention provides an expression vector for the biosynthesis of 6-aminocaproic acid comprising HpaI-HpaH gene, nemA gene, KIVD (alpha-ketoisovalerate decarboxylase) gene, and at least one of PdAT (beta-alanine-pyruvate transaminase) and BcAT (adenosylmethionine-8-amino-7-oxononanoate aminotransferase).

Figure 2:
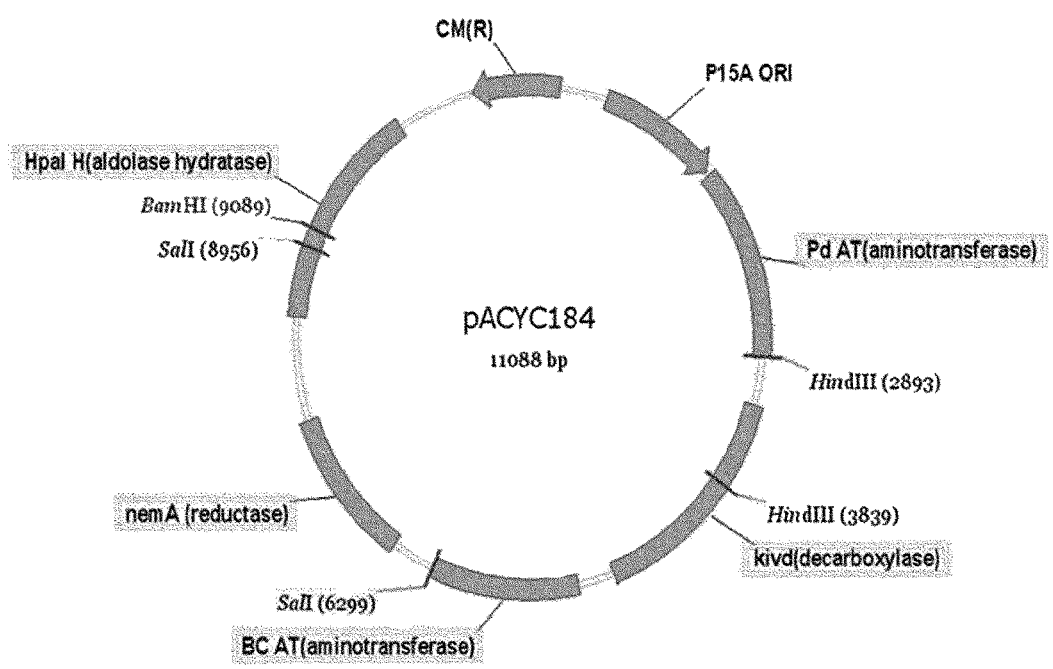
FIG. 2 is a pACYCWG vector map comprising HpaI (4-hydroxy-2-oxoheptane-1,7-dioate aldolase), HpaH (2-oxohept-3-ene-1,7-dioate dehydratase), nemA (N-ethylmaleimide reductase), KIVD (alpha-ketoisovalerate decarboxylase), PdAT (beta-alanine-pyruvate transaminase), and BcAT (adenosylmethionine-8-amino-7-oxononanoate aminotransferase) genes.

The expression vector may preferably be pACYCWG illustrated in FIG. 2, but is not limited thereto.

The recombinant vector of the present invention may be obtained by inserting the genes or fragments thereof into the expression vector via a general cloning method (Sambrook et al., 2nd ed., Cold Spring Harbor Laboratory, Cold Spring Harbor Laboratory Press, Cold Spring Harbor, N.Y., 1989). Specifically, an appropriate adaptor may be connected to a gene construct in order to facilitate the cloning of the gene construct.

The terms "vector", "expression vector", or "recombinant vector" are used to refer to DNA fragment(s) and nucleic acid molecules that transfer into cells. Vectors can duplicate DNA and can be reproduced independently in host cells. The vectors may refer to recombinant DNA molecules including proper nucleic acid sequences essential for expressing coding sequences operably linked to target coding sequences in specific host organisms. Promoters, enhancers, termination signals, and polyadenylation signals which can be used in cells of microorganisms are known in the art.

The vector of the present invention may typically be constructed as a vector for cloning or expression. Also, the vector of the present invention may be constructed with prokaryotic cells or eukaryotic cells serving as host cells. For example, in a case in which the recombinant vector of the present invention is an expression vector with prokaryotic cells serving as a host cell, it is common to include strong promoters (e.g. pLλ promoter, trp promoter, lac promoter, T7 promoter, tac promoter, etc.), ribosome binding sites, and transcription/translation termination sequences for initiation of translation.

Meanwhile, the vector that can be used in the present invention may be constructed by manipulating plasmids (e.g. pSC101, ColE1, pBR322, pUC8/9, pHC79, pGEX series, pET series, pACYC184, pUC19, etc.), phages (e.g. λgt4~λB, λ-Charon, λΔz1, M13, etc.), or viruses (e.g. SV40, etc.) often used in the art.

The expression vector may preferably include at least one selective marker. The marker, which is generally a nucleic acid sequence having properties that can be selected by a chemical method, include every gene that can distinguish a transformed cell from a non-transformed cell. The examples thereof include herbicide-resistant genes such as glyphosate, glufosinate ammonium, or phosphinothricin, and antibiotic-resistant genes such as kanamycin, G418, bleomycin, hygromycin, and chloramphenicol, but are not limited thereto.

In the vector of the present invention, a promoter may be promoters of CaMV 35S, actin, ubiquitin, pEMU, MAS, or histone, but is not limited thereto. The term "promoter" may refer to an upstream region of DNA in a gene structure and DNA molecules where RNA polymerase binds to initiate transcription. A "constitutive promoter" is a promoter that is active under most environmental conditions and developmental states, or during cell differentiation. As a transformant may be selected by various tissues in various steps, the constitutive promoter may be preferred in the present invention. Therefore, the constitutive promoter may be selected without limitation.

In the vector of the present invention, a general terminator may be used, and the examples thereof include nopaline synthase (NOS), rice α-amylase RAmy1 A terminator, phaseoline terminator, terminator of octopine gene of *Agrobacterium tumefaciens*, etc., but are not limited thereto.

Also, the present invention provides a transformant as the recombinant vector described above.

The transformant may preferably be selected from the group consisting of bacteria, yeasts, and fungi, more preferably, it may be bacteria, and most preferably it may be *E. coli*, but is not limited thereto.

The transformant may convert pyruvate and/or succinic semialdehyde (SSA) to 6-aminocaproic acid, but is not limited thereto.

In order to carry the vector of the invention into a host cell, the vector may be injected into a host cell by microinjection, calcium phosphate precipitation, electroporation, liposome-mediated transfection, *Agrobacterium*-mediated transfection, DEAE-dextran treatment, gene bombardment, etc.

Further, the present invention provides a method for producing caprolactam further including transforming 6-aminocaproic acid produced by the method for producing 6-aminocaproic acid to caprolactam.

Figure 9:
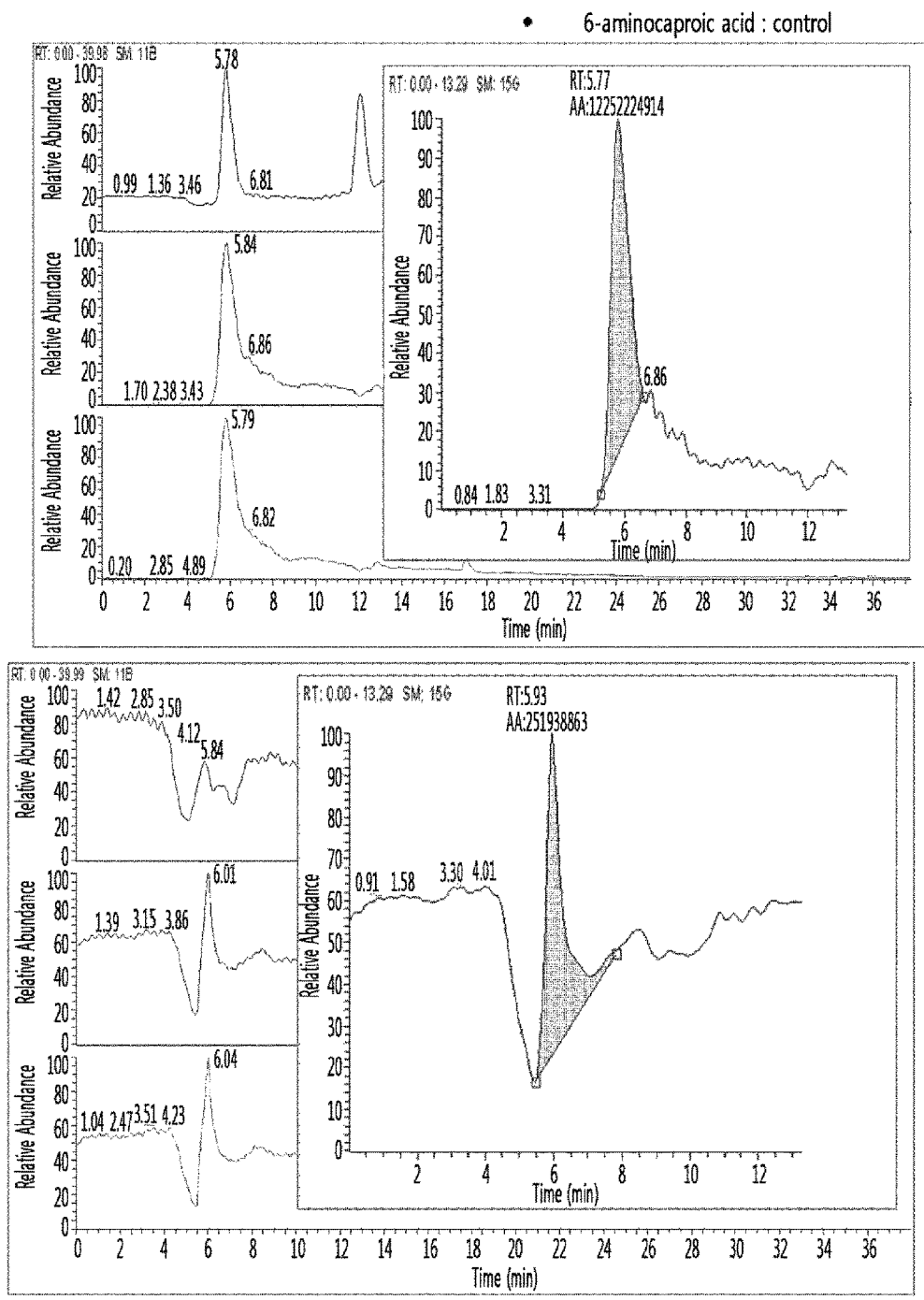
FIG. 9 is graphs showing LC-MS/MS results of biosynthetic activity of 6-aminocaproic acid from E. coli, which is transformed into pACYCWG vector comprising all genes of the present invention;
    first chromatogram: total ion current plot (TIC);
    second chromatogram: selected ion monitoring (SIM); and
    third chromatogram: selected reaction monitoring (SRM).
Figure 10:
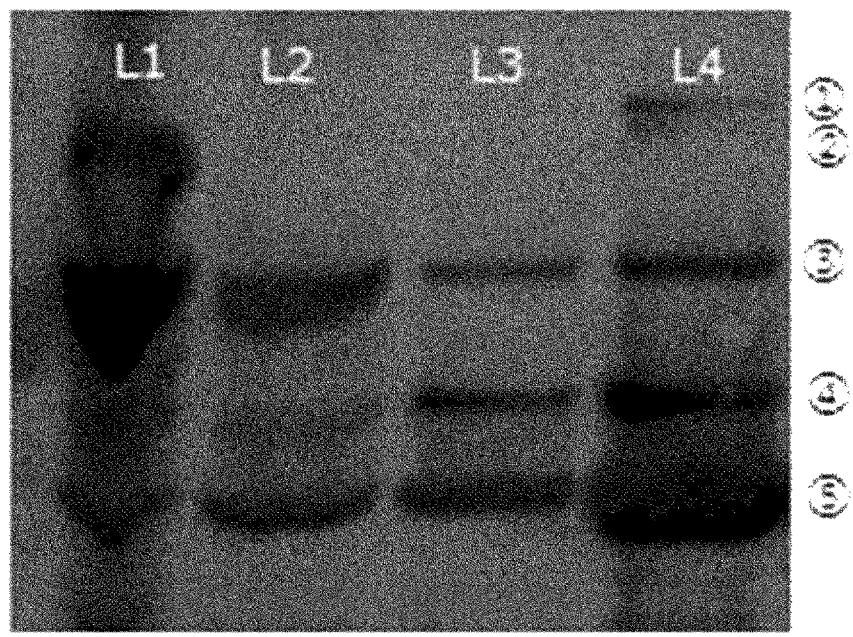
FIG. 10 shows a western blot image of expression of all enzymes cloned in the vector;
    L1: pACYCWG total proteins;
    L2: pACYCWG water soluble proteins;
    L3: pACYCWG purified proteins, diluted by 1/5;
    L4: pACYCWG purified proteins;
    (1): aldolase-dehydratase (HpaI-HpaH)-58KD;
    (2): decarboxylase (KIVD)-55KD;
    (3): aminotransferase 1 (PdAT)-46KD;
    (4): reductase (nemA)-40KD; and
    (5): aminotransferase 1 (BcAT)-38KD.

In a specific embodiment of the present invention, the present inventors isolated HpaI gene encoding aldolase, HpaH gene encoding dehydratase, nemA gene encoding reductase, KIVD gene encoding decarboxylase, and BcAT and PdAT genes encoding transaminase, which are enzymes related to the biosynthetic pathway of 6-aminocaproic acid (FIG. 1), a precursor of caprolactam, and had them introduced into vectors. Also, all genes were ligated from the vectors and introduced into one vector (FIG. 2). Further, enzymatic activities were confirmed by reactions of each enzyme expressed from the genes in the reaction pathway of pyruvate and/or succinic semialdehyde→2-oxohept-3-enedioic acid→2-ketopimelic acid→adipate semialdehyde→6-aminocaproic acid, or combinations of the enzymes (FIGS. 3 to 8). Furthermore, the biosynthesis of 6-aminocaproic acid was confirmed in *E. coli* in which vectors introduced with all the genes above were transformed (FIGS. 9 and 10).

Therefore, as the biosynthesis of 6-aminocaproic acid, which is a precursor of caprolactam, is possible in the transformant which is transformed into the vector in which the genes of the present invention are introduced, the transformant can be used in the biosynthesis of 6-aminocaproic acid.

Hereinafter, the present invention will be described in more detail with reference to the following examples to have a better understanding of the present invention. However, the following examples are provided for illustrative purposes only, and the scope of the present invention should not be limited thereto in any manner. The examples of the present invention are provided in order to fully describe the invention to those skilled in the art.

MODE FOR INVENTION

<Example 1> Cloning of Genes Encoding Enzymes in the Biosynthetic Pathway of 6-Aminocaproic Acid and Construction of Vectors <1-1> Cloning of Each Enzyme The genes encoding enzymes in the pathway biosynthesizing 6-aminocaproic acid from pyruvate were cloned from *E. coli*.

Specifically, HpaI gene (SEQ ID NO: 1) encoding aldolase, which converts pyruvate and/or succinic semialdehyde to 4-hydroxy-2-oxoheptanedioic acid; HpaH gene (SEQ ID NO: 2) encoding dehydratase, which converts 4-hydroxy-2-oxoheptanedioic acid to 2-oxohept-3-enedioic acid; nemA gene (SEQ ID NO: 4) encoding reductase, which converts 2-oxohept-3-enedioic acid to 2-ketopimelic acid; KIVD (alpha-ketoisovalerate decarboxylase) gene (SEQ ID NO: 5) encoding decarboxylase, which converts 2-ketopimelic acid to adipate semialdehyde; and PdAT (beta-alanine-pyruvate transaminase) gene (SEQ ID NO: 6) and BcAT (adenosylmethionine-8-amino-7-oxononanoate aminotransferase) gene (SEQ ID NO: 7) encoding transaminase, which convert adipate semialdehyde to 6-aminocaproic acid from *E. coli* described in Table 1 below, were amplified using primers (SEQ ID NOs: 15 to 26) described in Table 2, respectively, using PCR (95° C., 30 seconds, [95° C., 30 seconds, TM value for each primer: 30 seconds and 72° C., 60 seconds, total 30 cycles], 72° C., 5 minutes). Among the primers in Table 2, the parts written in italic refer to restriction enzyme sites, and the primers that were introduced into an In-Fusion™ Advantage PCR cloning kit (Clontech, USA) are underlined. After the amplification, HpaI and HpaH were ligated to be co-expressed using a ligase, and were assigned as HpaI-HpaH (SEQ ID NO: 3). The PCR products which were amplified above, having a ligase, were introduced into PET28(b+) vector decomposed by restriction enzymes (NdeI and BamHI), and the expression vectors introduced were assigned as pETHpaI, pETHpaH, pETnemA, pET-KIVD, pETBcAT, and pETPdAT (Table 4).

TABLE 1

| Strains | |
|---|---|
| DH5α | *E. coli* strain used for standard cloning procedures |
| BL21 (DE3) | *E. coli* strain used for heterologous gene expression |
| MG1655 (DE3) | *E. coli* strain used for heterologous gene expression |

TABLE 2

| Amplified genes | Directions[1] | Primers | SEQ ID NOs: | Sequence (5'-3') | Source |
|---|---|---|---|---|---|
| HpaI | F | hpaI_F | 15 | CGCGCGGCAGC*CATATG*ATGGAAAACAGTTTTAAAGCGGCGC | *Escherichia coli* w3110 |
|  | R | hpaI_R | 16 | GGTGGTGGTG*CTCGAG*ATACACGCCGGGCTTAATCGCT |  |
| HpaH | F | hpaH_F | 17 | CGCGCGGCAGC*CATATG*ATGTTCGACAAACACACCCACACC | *Escherichia coli* w3110 |
|  | R | hpaH_R | 18 | GGTGGTGGTG*CTCGAG*AACAAAGCGGCAGCTAATGGAGC |  |
| nemA | F | nemA_F | 19 | CGCGCGGCAGC*CATATG*ATGTCATCTGAAAAACTGTATTCCCC | *Escherichia coli* w3110 |
|  | R | nemA_R | 20 | GGTGGTGGTG*CTCGAG*CAACGTCGGGTAATCGGTATAGC | *Escherichia coli* w3110 |
| KIVD | F | KIVD_F | 21 | *CGCGCGGCAGCCATATG*ATGTATACAGTAGGAGATTACCTATT | *Lactococcus lactis* KCTC3115 |
|  | R | KIVD_R | 22 | GGTGGTGGTG*CTCGAG*TGATTTATTTTGTTCAGCAAATAGTTT | *Lactococcus lactis* KCTC3115 |
| BcAT | F | BcAT_F | 23 | CGCGCGGCAGC*CATATG*ATGATCTATTTTGATAATAGTGCG | *Bacillus cereus* KCTC1012 |
|  | R | BcAT_R | 24 | GGTGGTGGTG*CTCGAG*CCTCATCACTTCATATAATTTTGG | *Bacillus cereus* KCTC3115 |
| PdAT | F | PdAT_F | 25 | CGCGCGGCAGC*CATATG*ATGAACCAACCGCAAAGC | *Paracoccus denificans* KCTC2528 |
|  | R | PdAT_R | 26 | GGTGGTGGTG*CTCGAG*GGCCACCTCGGCAAA | *Paracoccus denificans* KCTC2528 |

[1]F: forward primer, R: reverse primer

<1-2> Construction of Vector in which Genes Encoding Each Enzyme are Ligated

The vector including all HpaI, HpaH, nemA, KIVD, PdAT, and BcAT genes encoding the enzymes in the pathway biosynthesizing 6-aminocaproic acid from pyruvate was constructed.

Specifically, HpaI encoding aldolase and HpaH encoding hydratase were ligated to be expressed together using a ligase, and were assigned as pETHpaI-HpaH. Further, in order to insert the genes encoding the enzymes above into a vector, the expression vector prepared in Example <1-1> was used as a template, and PCR (95° C., 30 seconds, [95° C., 30 seconds and 72° C., 60 seconds, total 30 cycles], 72° C., 5 minutes) was conducted using each primer in Table 3 (SEQ ID NOs: 27 to 36). The parts of primers that were introduced into an In-fusion™ Advantage PCR cloning kit (Clontech, USA) are underlined. BcAT, which is a PCR product having a first ligase, was introduced into pACYC184 decomposed by restriction enzyme sphI. The vector in which BcAT was introduced was then decomposed by HindIII, and PdAT, a PCR product, was introduced thereto. Furthermore, the vector in which BcAT and PdAT were introduced was decomposed by SalI, and KIVD, a PCR product, was introduced. Furthermore, the vector in which BcAT, PdAT, and KIVD were introduced was decomposed by BamHI, and nemA, a PCR product, was introduced. Lastly, the vector in which all the enzymes above introduced was decomposed by AhdI, and HpaI-HpaH, a PCR product, was introduced.

As a result, the expression vector including all genes HpaI-HpaH (ligation of HpaI and HpaH), nemA, KIVD, PdAT, and BcAT encoding enzymes in the biosynthesis pathway of 6-aminocaproic acid was prepared, and was assigned as pACYCWG (Table 4 and FIG. 2).

TABLE 3

| Amplified genes | Directions[1] | Primers | SEQ ID NOs: | Sequence (5'-3') | Source |
|---|---|---|---|---|---|
| pACYC HpaI-H | F | pACYC hpaIH_F | 27 | CGATACTATGACTGATAATACGACTCACTATAGGGGAATTG | pETI-H vector |
|  | R | pACYC hpaIH_R | 28 | CATGGCGTTGACTCTCAAAAAACCCCTCAAGACCC | pETI-H vector |

TABLE 3 -continued

| Amplified genes | Directions[1] | Primers | SEQ ID NOs: | Sequence (5'-3') | Source |
|---|---|---|---|---|---|
| pACYC nemA | F | pACYC nemA_F | 29 | CCCGTCCTGTGGATGTAATACGACTCACTA TAGGGGAATTG | pETnemA vector |
| | R | pACYC nemA_R | 30 | CCGGCGTAGAGGATCCAAAAAACCCCTCAA GACCC | pETnemA vector |
| pACYC kivd | F | pACYC KIVD_F | 31 | AAGGGAGAGCGTCGATAATACGACTCACTA TAGGGGAATTG | pETKIVD vector |
| | R | pACYC KIVD_R | 32 | AAGGGCATCGGTCGACAAAAAACCCCTCAA GACCC | pETKIVD vector |
| pACYC BcAT | F | pACYC BcAT_F | 33 | CCATCTCCTTGCATGTAATACGACTCACTA TAGGGGAATTG | pETBcAT vector |
| | R | pACYC BcAT_R | 34 | AAGGAATGGTGCATGCAAAAAACCCCTCAA GACCC | pETBcAT vector |
| pACYC PdAT | F | pACYC PdAT_F | 35 | TATCATCGATAAGCTTAATACGACTCACTA TAGGGGAATTG | pETPdAT vector |
| | R | pACYC PdAT_R | 36 | TACCGCATTAAAGCTCAAAAAACCCCTCAA GACCC | pETPdAT vector |

TABLE 4

| Plasmids | Description | Source |
|---|---|---|
| pETI-H | PT7, His-tag, kanr; E. coli expression vector carrying aldolase | |
| pETnemA | PT7, His-tag, kanr; E. coli expression vector carrying reductase | |
| pETKIVD | PT7, His-tag, kanr; E. coli expression vector carrying decarboxylase | |
| pETBcAT | PT7, His-tag, kanr; E. coli expression vector carrying transaminase | |
| pETPdAT | PT7, His-tag, kanr; E. coli expression vector carrying transaminase | |
| pACYC184 | E. coli cloning vector | Mo-bi tec |
| pACYCWG | E. coli cloning vector carrying whole genes containing PT7 | |

<Example 2> Confirmation of Each Enzyme and Fusion Protein

<2-1> Expression and Purification of Each Enzyme and Fusion Protein

Figure 7:
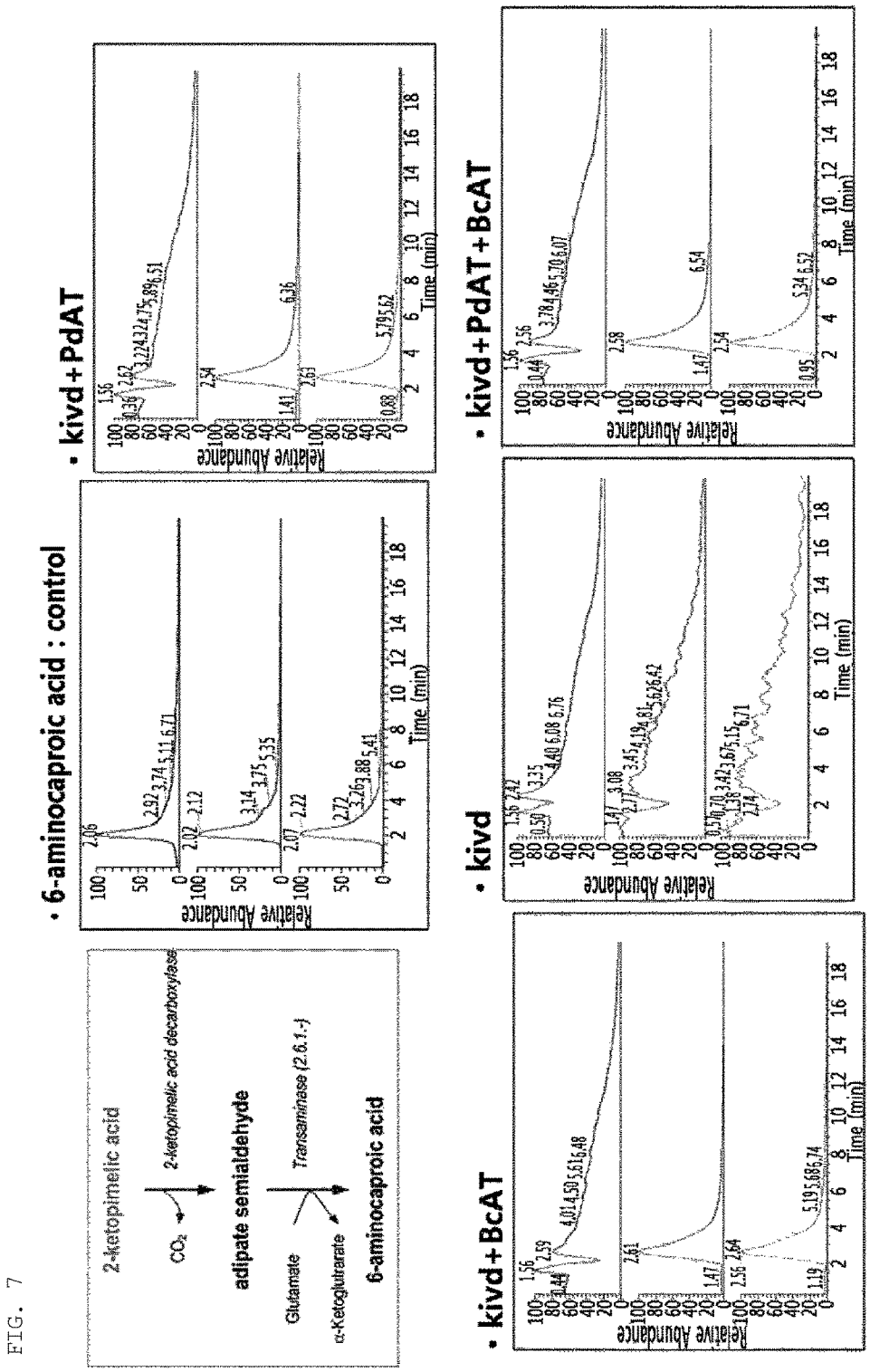
FIG. 7 is graphs showing LC-MS/MS results of conversion of 2-ketopimelic acid to 6-aminocaproic acid by a coupling reaction of decarboxylase (KIVD) with transaminase (PdAT and/or BcAT);
    first chromatogram: total ion current plot (TIC);
    second chromatogram: selected ion monitoring (SIM); and
    third chromatogram: selected reaction monitoring (SRM).

The plasmids, namely, pETHpaI, pETHpaH, pETnemA, pETKIVD, pETBcAT, pETPdAT, pETHpaI-HpaH, and pACYCWG prepared in Example 1, were transformed into E. coli BL21(DE3) via thermal shock. The transformant was cultured in an LB medium containing 50 μg/mL of antibiotics at 37° C. When the culture solution of the transformant reached a concentration of A600=0.5, 0.5 mM of IPTG (isopropyl-β-thio-D-galactopyranoside) was added, and the resultant was further cultured for 3 hours at 37° C. The cultured cells were collected by centrifugation and the pellet produced was disrupted by sonication. After the disruption of pellet, HpaI (SEQ ID NO: 8), HpaH (SEQ ID NO: 9), HpaI-HpaH (SEQ ID NO: 10), nemA (SEQ ID NO: 11), KIVD (SEQ ID NO: 12), PdAT (SEQ ID NO: 13), and BcAT (SEQ ID NO: 14) were purified from the supernatant using Ni-NTA agarose (Qiage, Germany) and an Econo Pac Chromatography Column (Bio-Rad, USA) according to the manufacturer's description. The concentrations of purified proteins were measured by a BCA protein assay kit Pierce (USA), and as a result, the concentrations were HpaI-H: 0.216 mg/mL; Kivd: 0.523 mg/mL; PdAT: 0.176 mg/mL; BcAT: 0.632 mg/mL; nemA: 0.659 mg/mL, and protein purity was measured as shown in FIG. 7.

<Example 3> Confirmation of Activities of Purified Enzymes

<3-1> Confirmation of Activity of Purified Aldolase-Dehydratase (HpaI-HpaH)

An enzymatic reaction was carried out to confirm the conversion of pyruvate and/or succinic semialdehyde to 2-oxohept-3-enedioic acid by aldolase and aldolase-dehydratase (HpaI-HpaH) enzymes (purified using E. coli transformed into pETHpaI-HpaH) purified in Example 2-1.

Specifically, 4 g/L of pyruvate, 4 g/L of succinic semialdehyde (SSA), which are substrates, and 50 mM of $MnCl_2$, serving as a cofactor, were mixed together with aldolase, which is a protein expressing purified HpaI, and aldolase-dehydratase expressed by ligating HpaI and HpaH, both of which were purified in Example 2-1 above, respectively. The volume was then adjusted by 100 mM HEPES buffer (pH 8.0), and the reaction was carried out overnight at 30° C. After the reaction, the change in concentration of pyruvate, a substrate, was confirmed by measuring absorbance at $A_{570}$ using a pyruvate assay kit (Sigma, USA).

Figure 3:
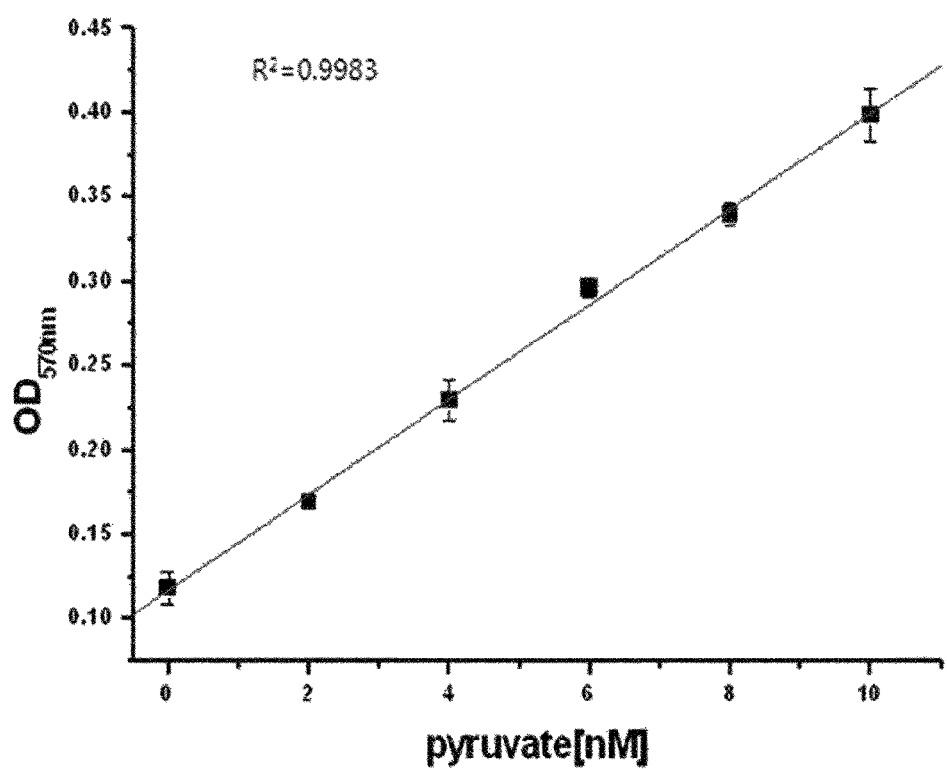
FIG. 3 is a standard curve showing changes in concentrations of pyruvate, which is a substrate, by an enzymatic reaction of aldolase-dehydratase (HpaI-HpaH).

As a result, it was confirmed that the concentration of pyruvate, a substrate for aldolase-hydratase (HpaI-HpaH), was reduced, implying that the conversion of pyruvate and/or succinic semialdehyde to 2-oxohept-3-enedioic acid was carried out (FIG. 3).

TABLE 5

| Aldolase-hydratase | Pyruvate | SSA | $A_{570}$ (absorbance) | Pyruvate [μM] |
|---|---|---|---|---|
| 0 | 100 | 100 | 0.603 | 3.42 |
| 300 | 0 | 0 | 0.162 | 1.22 |
| 300 | 100 | 100 | 0.184 | 1.33 |
| 100 | 100 | 100 | 0.322 | 2.01 |

<3-2> Confirmation of Activity of Purified Reductase (nemA)

An enzymatic reaction was carried out to confirm the conversion of 2-oxohept-3-enedioic acid to 2-ketopimelic acid by reductase (nemA) purified in Example 2-1.

Specifically, as it is difficult to purchase 2-oxohept-3-enedioic acid, a substrate, 2-ketopimelic acid was used as a substrate using the fact that the reaction is also carried out in the reverse direction. 4 mM of NAD, 0.4 mM of $FeSO_4$, which are cofactors, and reductase, in which nemA is expressed, were added to the substrate. The volume was then adjusted by 1 M potassium phosphate buffer (pH 5.3) to balance the pH, and the reaction was induced at 30° C. After the reaction, the amount of NADH produced during the conversion of NAD to NADH was measured as absorbance at $A_{450}$ using an NADH assay kit (abcam. USA), confirming the conversion effect (Table 6).

Figure 4:
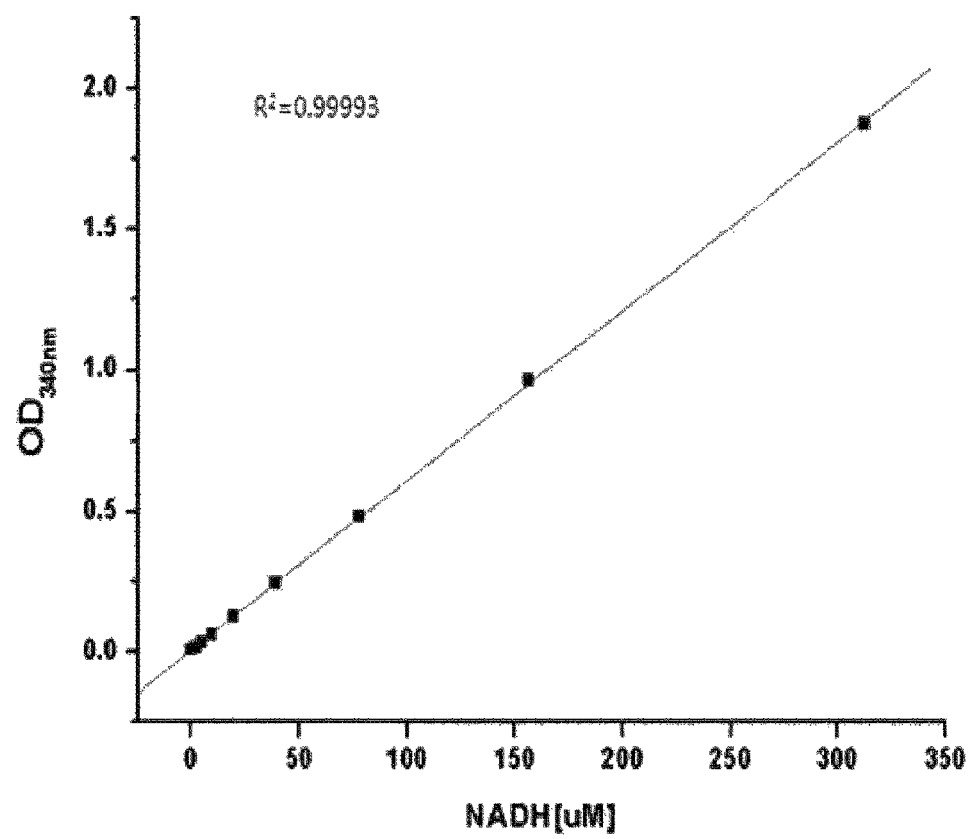
FIG. 4 is a standard curve showing changes in concentrations of NADH, which is a product, in a reverse reaction to confirm the enzymatic activity of reductase (nemA).

As a result, it was confirmed that the reductase, which was expressed and purified by pETnemA, produced NADH, confirming the conversion effect of 2-ketopimelic acid to 2-oxohept-3-enedioic acid (FIG. 4). The results of Examples 2 and 3 are summarized in Table 7.

TABLE 6

| Reductase | 2-Ketopimelic acid | NAD | $FeSO_4$ | nemA |
|---|---|---|---|---|
| 200 | 0 | 4 mM | 0.4 mM | 0.754 |
| 200 | 4 mM | 4 mM | 0.4 mM | 1.26 |
| 100 | 4 mM | 4 mM | 0.4 mM | 0.943 |
| 0 | 4 mM | 4 mM | 0.4 mM | 0.881 |

TABLE 7

| | Expression properties | Purity (%) | Specific activity (U/mg) | Assay |
|---|---|---|---|---|
| HpaI-HpaH | Soluble | 22 | 13.41 | Pyruvate |
| nemA | Soluble | 43 | 2.71 | NADH |
| KivD | Soluble | 24 | — | No STD |
| PdAT | Soluble | 84 | 13.13 | Glutamate |

<3-3> Analysis of Coupling Reaction of Aldose-Dehydratase with Reductase

The conversion of pyruvate and/or succinic semialdehyde to 2-oxohept-3-enedioic acid was confirmed in Example 3-1, and the conversion of 2-oxohept-3-enedioic acid to 2-ketopimelic acid was confirmed in Example 3-2 via the reverse reaction. Herein, it was confirmed whether two reactions occur simultaneously by the two enzymes.

Specifically, 4 g/L of pyruvate, 4 g/L of SSA, and 200 mM of NADH were added as substrates, and 50 mM of $MnCl_2$ was added thereto as a cofactor. Aldolase-hydratase, in which HpaI-HpaH is expressed, and reductase, in which nemA is expressed, were then added thereto, and the volume thereof was adjusted by 100 mM potassium phosphate buffer to balance the pH. Subsequently, an enzymatic reaction was induced to confirm 2-ketopimelic acid, which is a product, using LC-MS/MS. TIC indicates the overall isolation from 50 m/z to 300 m/z, SIM is a method for separately monitoring peaks of molecular ions (herein, 155) invisible in full scan, and SRM is a method for producing daughter ions from the molecular ions by splitting the same at high energy.

Figure 5:
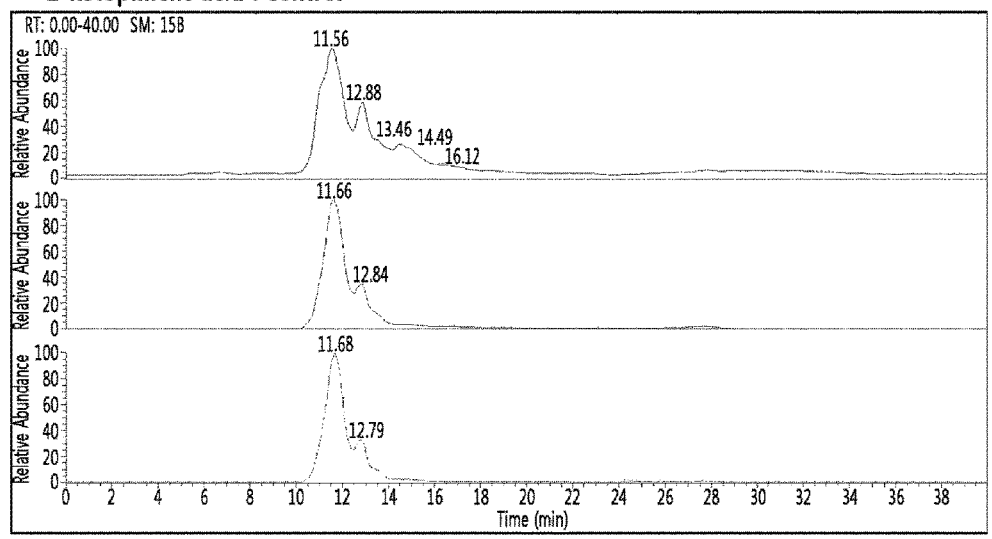
FIG. 5 is graphs showing LC-MS/MS results of 2-ketopimelic acid formation by a coupling reaction of aldolase-dehydratase (HpaI-HpaHHpaH) with reductase (nemA);
    first chromatogram: total ion current plot (TIC);
    second chromatogram: selected ion monitoring (SIM); and
    third chromatogram: selected reaction monitoring (SRM).
Figure 5:
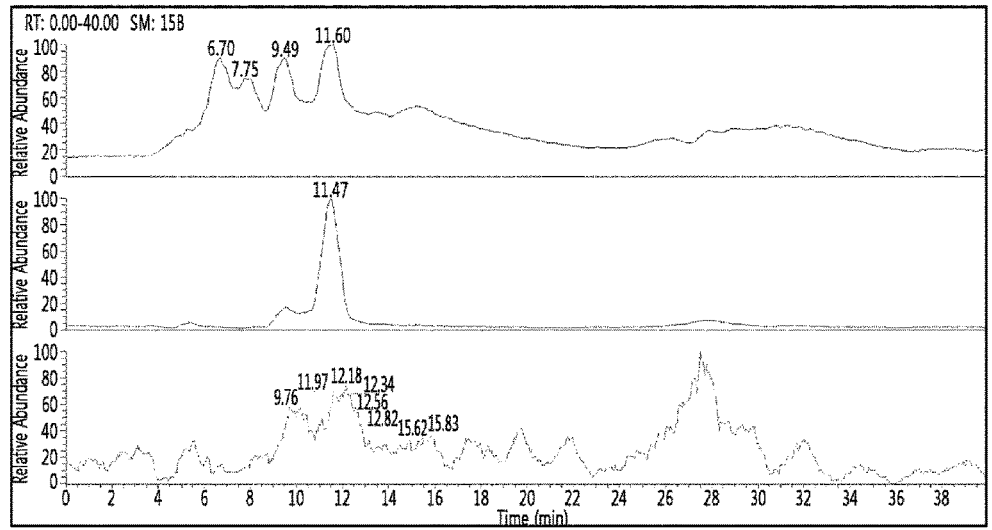

As a result, peaks were formed at similar times with 2-ketopimelic acid (Sigma Aldrich), which is a control group, and the mass of peaks was identical (FIG. 5). Therefore, if the two enzymes are co-expressed, 2-ketopimelic acid is produced from pyruvate and/or succinic semialdehyde.

<3-4> Confirmation of Activity of Purified Transaminase (BcAT or PdAT)

An enzymatic reaction was carried out to confirm the conversion of adipate semialdehyde to 6-aminocaproic acid by the transaminase purified in Example 2-1.

Specifically, as it was difficult to purchase adipate semialdehyde, which is a substrate, 20 mM of 6-aminocaproic acid was added as a substrate using the fact that the reaction also occurs in the reverse direction. 10 mM of sodium alpha-ketoglutarate was then added thereto as an amino group donor, 0.2 mM of PLP was added thereto as a cofactor, and subsequently, transaminase, in which BcAT and PdAT were expressed and purified in Example 2-1, was added thereto. The volume thereof was adjusted by 100 mM potassium phosphate buffer (pH 7.0) to balance the pH. The enzymatic reaction was carried out overnight at 30° C., and the formation of glutamate, a product, and a change in concentrations was measured via glutamate analyzer to confirm the reaction, and a specific activity was then calculated.

As a result, it was confirmed that glutamate was formed in both PdAT and BcAT, and the activity of glutamate was higher in PdAT (Table 8).

TABLE 8

| | Glutamate (mM) | Specific activity (U/mg) |
|---|---|---|
| pETPdAT | 1.40 | 13.13 |
| pETcAT | 0.56 | 3.55 |

<3-5> Analysis of Coupling Reaction of Transaminase (BcAT and/or PdAT) with Decarboxylase (KIVD)

Herein, it was confirmed whether 2-ketopimelic acid was converted to 6-aminocaproic acid by transaminase (BcAT and/or PdAT), confirmed in Example 3-4, and decarboxylase (KIVD) of the present invention.

Specifically, 2-ketopimelic acid as a substrate, 20 mM of glutamate as an amino group donor, 5 mM of $MgSO_4$ as a cofactor, and 0.1 mM of PLP were added to confirm whether the two reactions occur simultaneously. Decarboxylase, in which KIVD was expressed and purified, and transaminase, in which BcAT and PdAT were expressed and purified, were then added thereto, and the volume of the resultant was adjusted by 100 mM potassium phosphate buffer (pH 7.0) to balance the pH. The enzymatic reaction was induced overnight at 30° C., and a product was obtained.

To confirm the product by TLC, the underside of a silica gel plate was marked by pencil with a line at the 1 cm point and with a dot where the sample was to be loaded. The thus-obtained product was loaded onto the plate by 1 µL drops a total of 5 times, the plate was inserted into a tank after drying, and the entrance was sealed to develop the plate for 1 hour. The developing reagent was mixed at a ratio of 5:1:5 between n-butanol:acetic acid:D.W., and only the supernatant was used. After the development of the plate, the plate was removed, sprayed with a 1% ninhydrin solution, and placed back into the tank for 5 minutes at 80° C. to confirm the color of the spots.

Also, the product was confirmed by LC-MS/MS (column: 250 mm×4.6 mm OptimaPak C18 (RS Tech, Korea); mobile phase: A—20% acetonitrile, B—80% distilled water; velocity: 300 µL/min; load amount: 1 µL; ionization: ESI(+)-MS, positive scan mode; source voltage=2.5 kV; capillary temperature=350° C.; m/z=50 to 150; step size=0.1 m/z; nebulizer pressure=100 psi).

Figure 6:
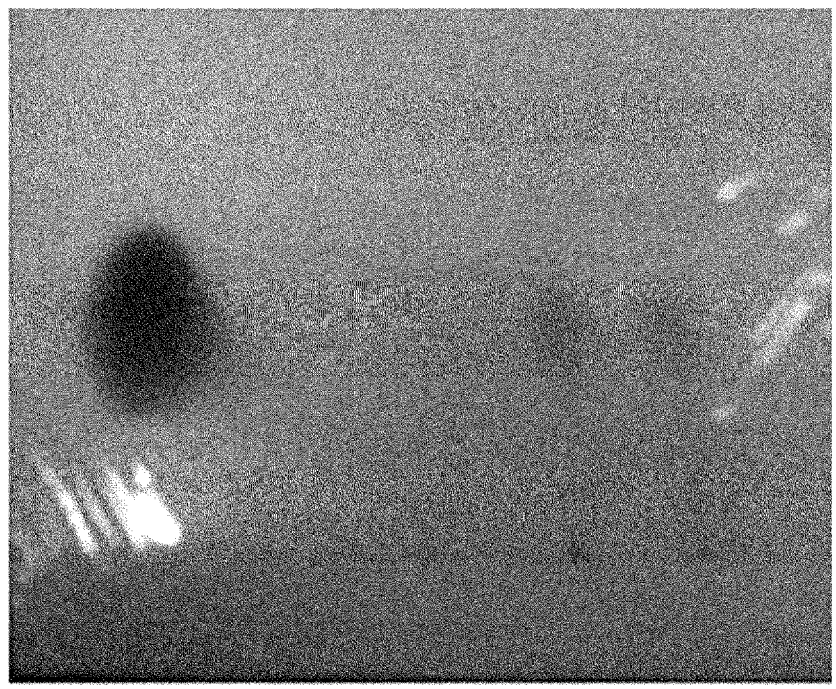
FIG. 6 is an image showing TLC results of conversion of 2-ketopimelic acid to 6-aminocaproic acid by a coupling reaction of decarboxylase (KIVD) with transaminase (PdAT and/or BcAT);
    L1: 1 M 6-aminocaproic acid;
    L2: negative control group (chemical blank);
    L3: negative control group (biological blank with KIVD-His);
    L4: KIVD-PdAT; and
    L5: KIVD-PdAT-BcAT.

As a result, it was confirmed by TLC and LC-MS/MS that 6-aminocaproic acid was produced (FIGS. 6 and 7).

<Example 4> Confirmation of Biosynthesis of 6-Aminocaproic Acid and Enzymatic Activity in Cells

<4-1> Confirmation of Biosynthesis of 6-Aminocaproic Acid

Herein, the biosynthesis of 6-aminocaproic acid from glucose and SSA was confirmed by the expression of fusion protein (aldolase-dehydratase-reductase-decarboxylase-transaminase) transformed into pACYCWG in *E. coli* in Example 1-2 above.

Specifically, in 2 L of medium containing the components shown in Table 9, *E. coli* transformed into pACYCWG and *E. coli* transformed into an empty vector, which is a control group, were cultured in a fed-batch culture for 24 hours at 37° C.

After culturing, cells were subjected to centrifugation to obtain a pellet, and the pellet was washed with distilled water five times and suspended in 50 mL of distilled water. 10 g of glucose, 4 g/L of succinic semialdehyde, and 1 mL/L of trace elements were added to the suspension, and an in vivo reaction was induced for 16 hours at 37° C. After the reaction, 6-aminocaproic acid was confirmed by TLC and LC-MS (column: 250 mm×4.6 mm OptimaPak C18 (RS Tech, Korea); mobile phase: A—20% acetonitrile, B—80% distilled water; velocity: 300 μL/min; load amount: 1 μL; ionization: ESI(+)-MS, positive scan mode; source voltage=2.5 kV; capillary temperature=350° C.; m/z=50 to 150; step size=0.1 m/z; nebulizer pressure=100 psi) by merely obtaining the supernatant. TIC indicates the overall isolation from 50 m/z to 300 m/z, SIM is a method for separately monitoring peaks of molecular ions (herein, 155) invisible in full scan, and SRM is a method for producing daughter ions from the molecular ions by splitting the same at high energy.

Figure 8:
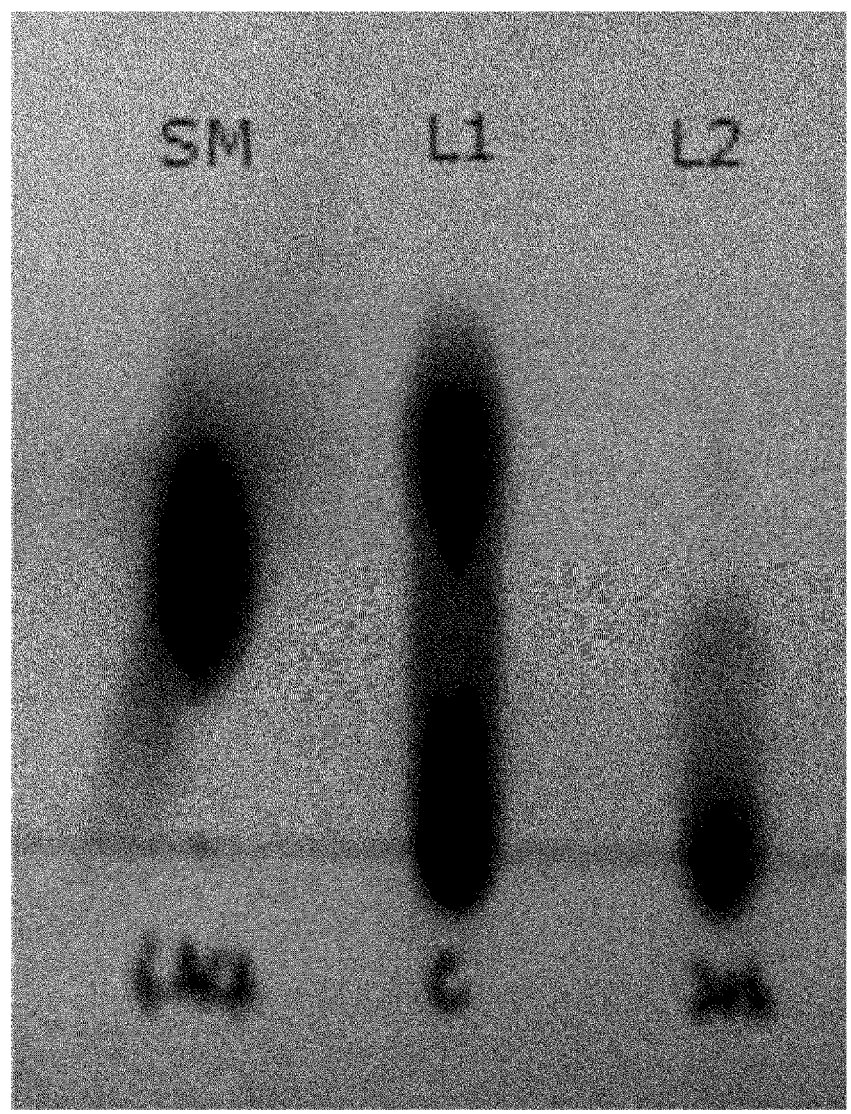
FIG. 8 is an image showing TLC results of biosynthetic activity of 6-aminocaproic acid from E. coli, which is transformed into pACYCWG vector comprising all genes of the present invention;
    SM: 6-aminocaproic acid;
    L1: negative control group (pACYC184); and
    L2: response group pACYCWG.

As a result, lane #3, in which the biosynthetic conversion was induced with cells cultured for 20 hours, showed a spot on the same line as 6-aminocaproic acid, confirming that 6-aminocaproic acid was produced (FIG. 8). Also, peaks of 6-aminocaproic acid were confirmed in the results measured with LC-MS and LC-MS/MS, confirming the biosynthetic pathway thereof in vivo (FIG. 9).

TABLE 9

| Component | g/L |
| --- | --- |
| Glucose | 15 |
| $MgSO_4 \cdot 7H_2O$ | 2 |
| Yeast extract | 5 |
| $(NH_4)_2SO_4$ | 10 |
| NaCl | 0.5 |
| Trace elements | 1 |
| $KH_2PO_4$ | 3 |
| $Na_2HPO_4 \cdot 12H_2O$ | 3 |
| Chloramphenicol | 0.01 |
| Lactose | 5 |

Also, to calculate a conversion yield from glucose to 6-aminocaproic acid (6-ACA), the amount of glucose used was measured by a glucose analyzer and the amount of 6-aminocaproic acid produced was calculated from LC-MS. During an actual reaction, 10 g of glucose was added, however, the actual amount of glucose used by the strain was calculated by the initial amount of glucose minus the final amount of glucose, and the amount of 6-ACA formed was measured with a quantitative value (no plasmid, Pacycl84, HpaIH-nemA, PdAT-Kivd: negative control group). As a result, it was confirmed that the conversion yield from glucose to 6-ACA was shown to be about 2.5% (Table. 10).

TABLE 10

| | Initial glucose (g/L) | Final glucose (g/L) | 6-ACA (g/L) |
| --- | --- | --- | --- |
| No plasmid | 10 | 9.87 | ND (not detected) |
| pACYC184 | 10 | 6.19 | ND |
| HpaIH-nemA | 10 | 6.23 | ND |
| PdAT-Kivd | 10 | 6.54 | ND |
| pACYCWG | 10 | 4.17 | ≈0.3 |

<4-2> Confirmation of Enzyme Expression in Cells

The fusion recombinant proteins in cells cultured in Example 4-1 were subjected to western blot analysis using SDS-PAGE according to Laemmli procedures (Laemmli, U. K. 1970, Nature 227:680-685).

Specifically, proteins isolated by 10% SDS-PAGE gel were transferred onto a nitrocellulose membrane. After the transfer, the nitrocellulose membrane was blocked with 5% PBS (phosphate buffered saline) containing dried skim milk and washed with PBST (0.1% Tween20 in PBS) three times. The thus-washed membrane was reacted with His-probe monoclonal antibodies (Santa Cruz Biotechnology, USA) for 1 hour. An antigen that specifically reacts with an IgG AP (alkaline phosphatase) antibody was then shown in an AP conjugate substrate kit (Bio-rad, USA) (FIG. 10).

<Example 5> Analysis of Fermentation Conditions for High Enzymatic Activity

<5-1> Culturing of Flask

A flask was cultured to analyze its culture medium in order to confirm whether 6-aminocaproic acid was produced from a culture supernatant of *E. coli* transformed into pACYCWG.

Specifically, in 100 mL of medium containing the components shown in Table 11, *E. coli* transformed into pACYCWG and *E. coli* transformed into an empty vector, which is a control group, were cultured for 24 hours at 28° C. After culturing of *E. coli*, the supernatant was obtained and analyzed by LC-MS.

Figure 11:
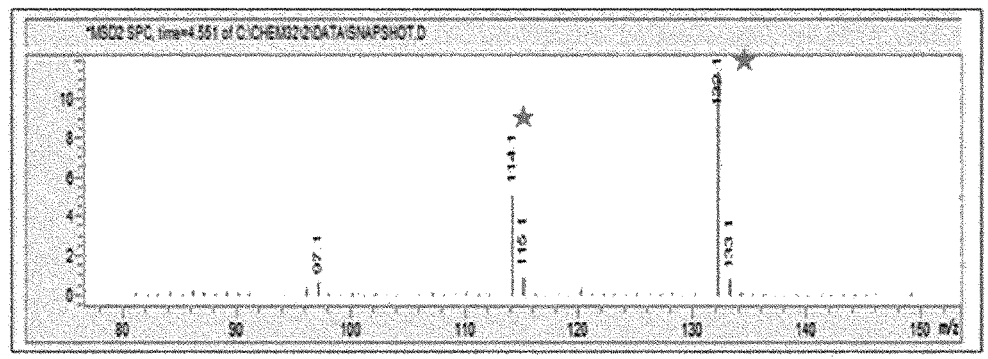
FIG. 11 is graphs showing LC-MS results of biosynthetic activity of 6-aminocaproic acid from E. coli, which is transformed into pACYCWG vector comprising all genes of the present invention.
Figure 11:
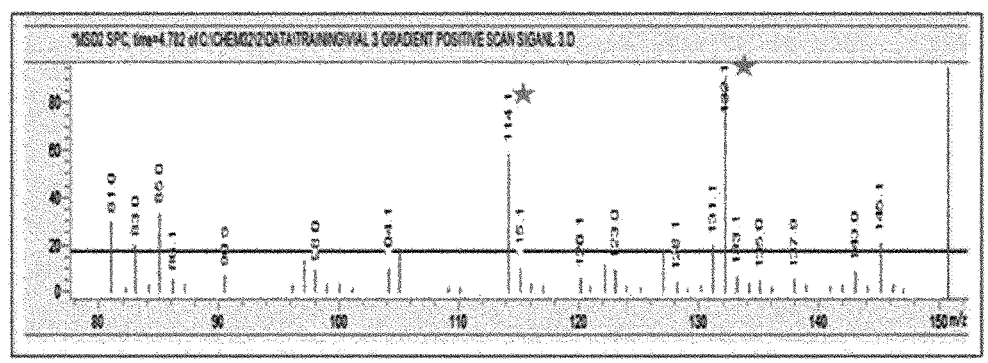
Figure 11:
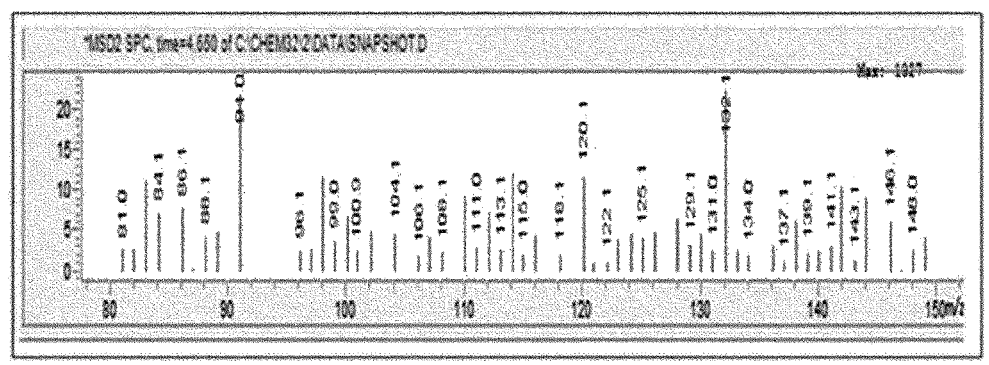

As a result, it was confirmed through an LC-MS spectrum that the biosynthetic conversion was induced (FIG. 11).

TABLE 11

| Component | g/L |
| --- | --- |
| Glucose | 15 |
| $MgSO_4 \cdot 7H2O$ | 2 |
| Yeast extract | 20 |
| Casein peptone | 10 |
| $(NH_4)_2SO_4$ | 10 |
| NaCl | 0.5 |
| Trace elements | 1 |
| $KH_2PO_4$ | 3 |
| $Na_2HPO_4 \cdot 2H_2O$ | 3 |
| Chloramphenicol | 0.01 |

<5-2> Fermentation Culture

Figure 12:
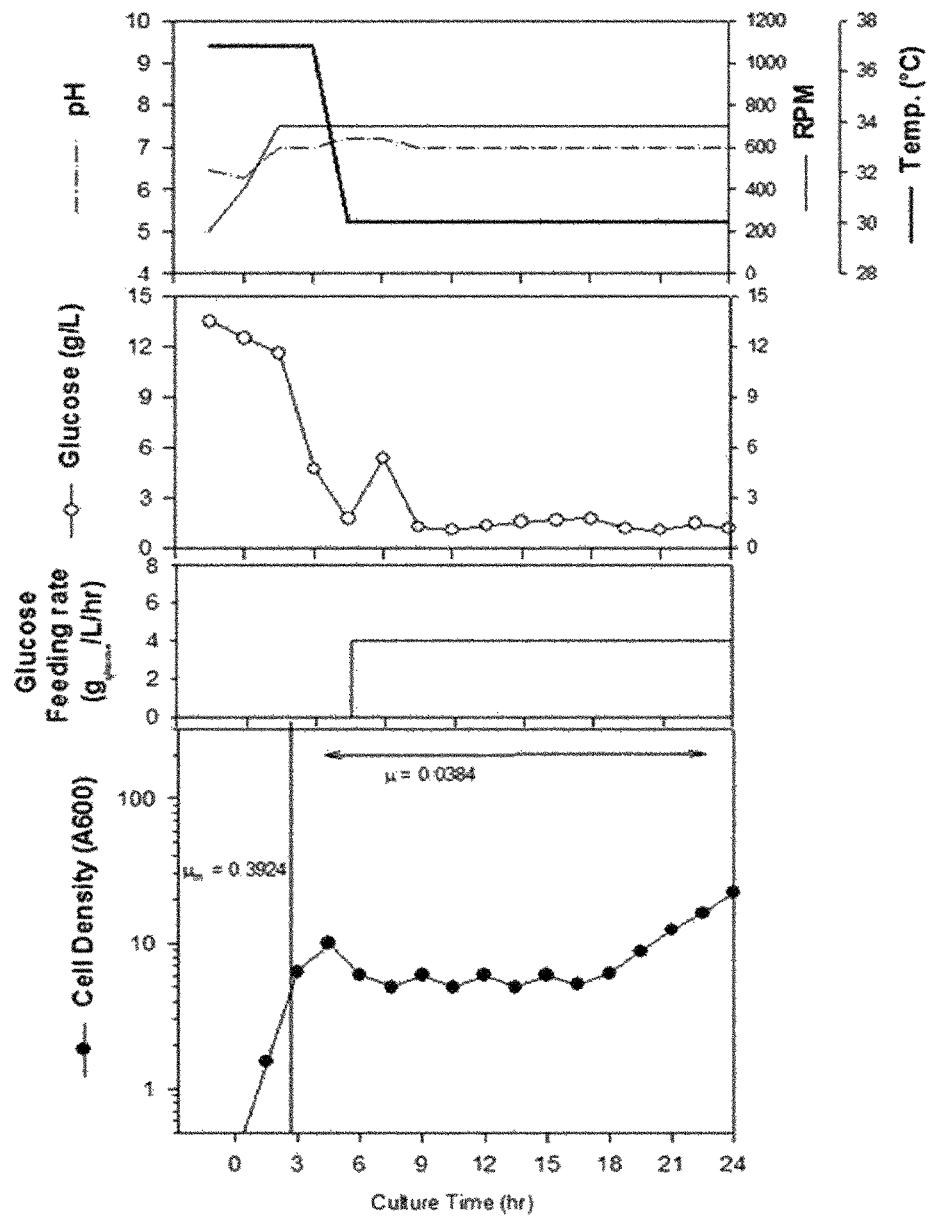
FIG. 12 is graphs showing fermentation of E. coli, which is transformed into pACYCWG vector in a fermentation medium experiment according to an embodiment of the present invention.
Figure 13:
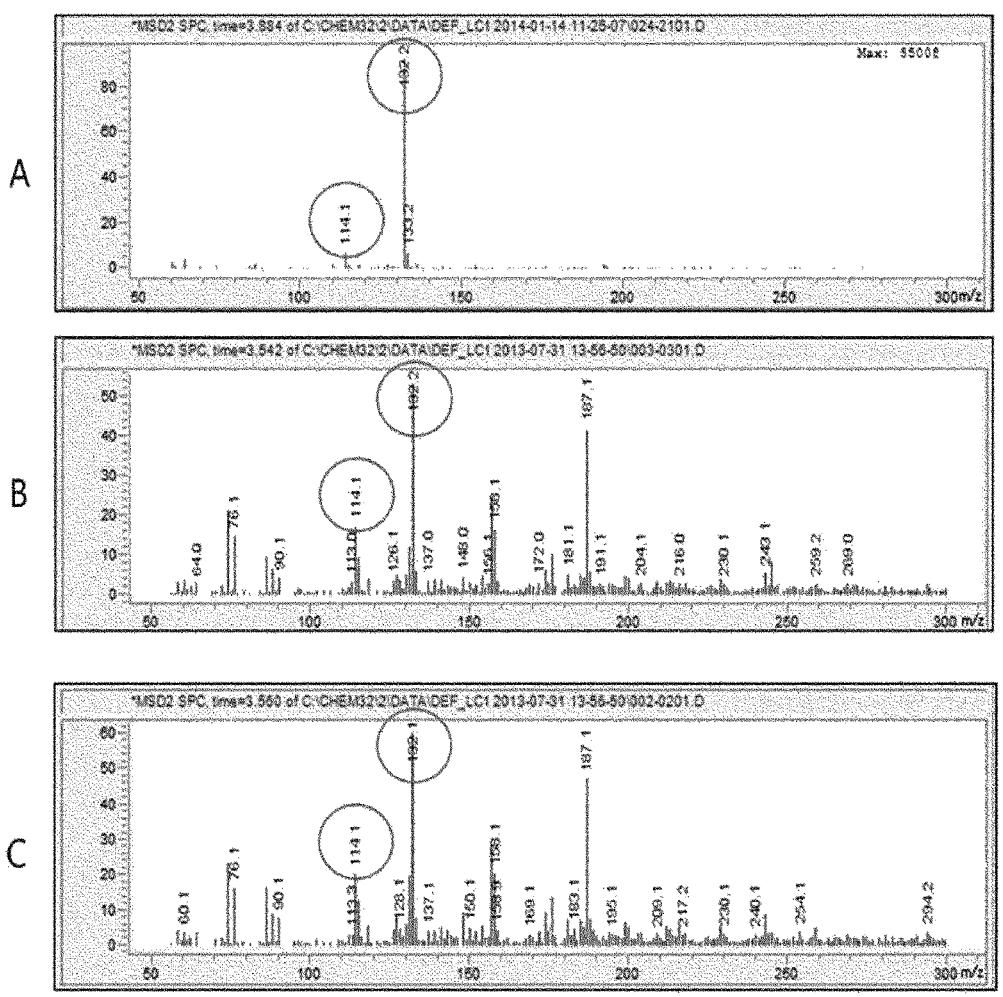
FIG. 13 is graphs showing LC-MS results of biosynthetic activity of 6-aminocaproic acid by culturing E. coli in the fermentation medium experiment according to an embodiment of the present invention, followed by obtaining a supernatant.

In 2.5 L of medium containing the components shown in Table 12, *E. coli* transformed into pACYCWG was cultured for 24 hours for mass culturing of 6-aminocaproic acid. After culturing, 15 g/L of lactose was added at the point when all of the initial glucose was consumed to induce the expression of enzymes, and then 4 g/L of glucose was fed each hour (FIG. 12). The supernatant was obtained and analyzed by LC-MS after culturing of *E. coli*. As a result, it was confirmed that 6-aminocaproic acid was produced (FIG.

Figure 14:
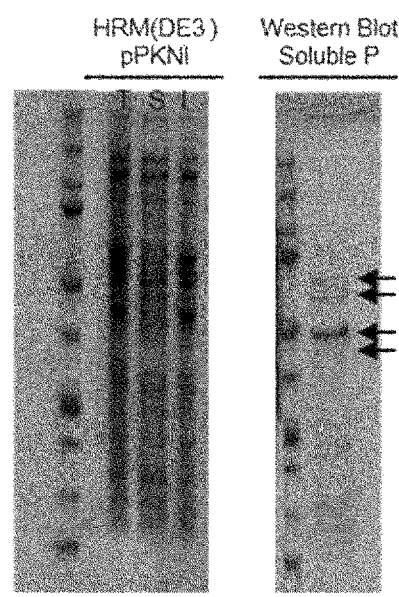
FIG. 14 shows a western blot image of all enzymes cloned into a vector in the fermentation medium experiment according to an embodiment of the present invention;
    (from top) first arrow: HpaI-H;
    second arrow: Kivd;
    third arrow: PdAT; and
    fourth arrow: nemA.

13). Also, it was confirmed that desired enzymes were expressed using fermentation culture via western blot (FIG. 14).

TABLE 12

| Component | g/L |
|---|---|
| Glucose | 15 |
| MgSO$_4$•7H2O | 2 |
| Yeast extract | 5 |
| (NH$_4$)$_2$SO$_4$ | 10 |
| NaCl | 0.5 |
| Trace elements | 1 |
| KH$_2$PO$_4$ | 1.6 |
| Na$_2$HPO$_4$•2H$_2$O | 4.4 |
| Chloramphenicol | 20 μg/mL |

<5-3> Strain Improvement

Until now, two types of transaminase were used. However, as poor expression levels were observed due to many enzymes, only one type of transaminase was used herein. PdAT having a high specific activity was used rather than BcAT to construct a vector, and the vector was assigned as pPKNI (pACYCWG-BcAT).

Figure 15:
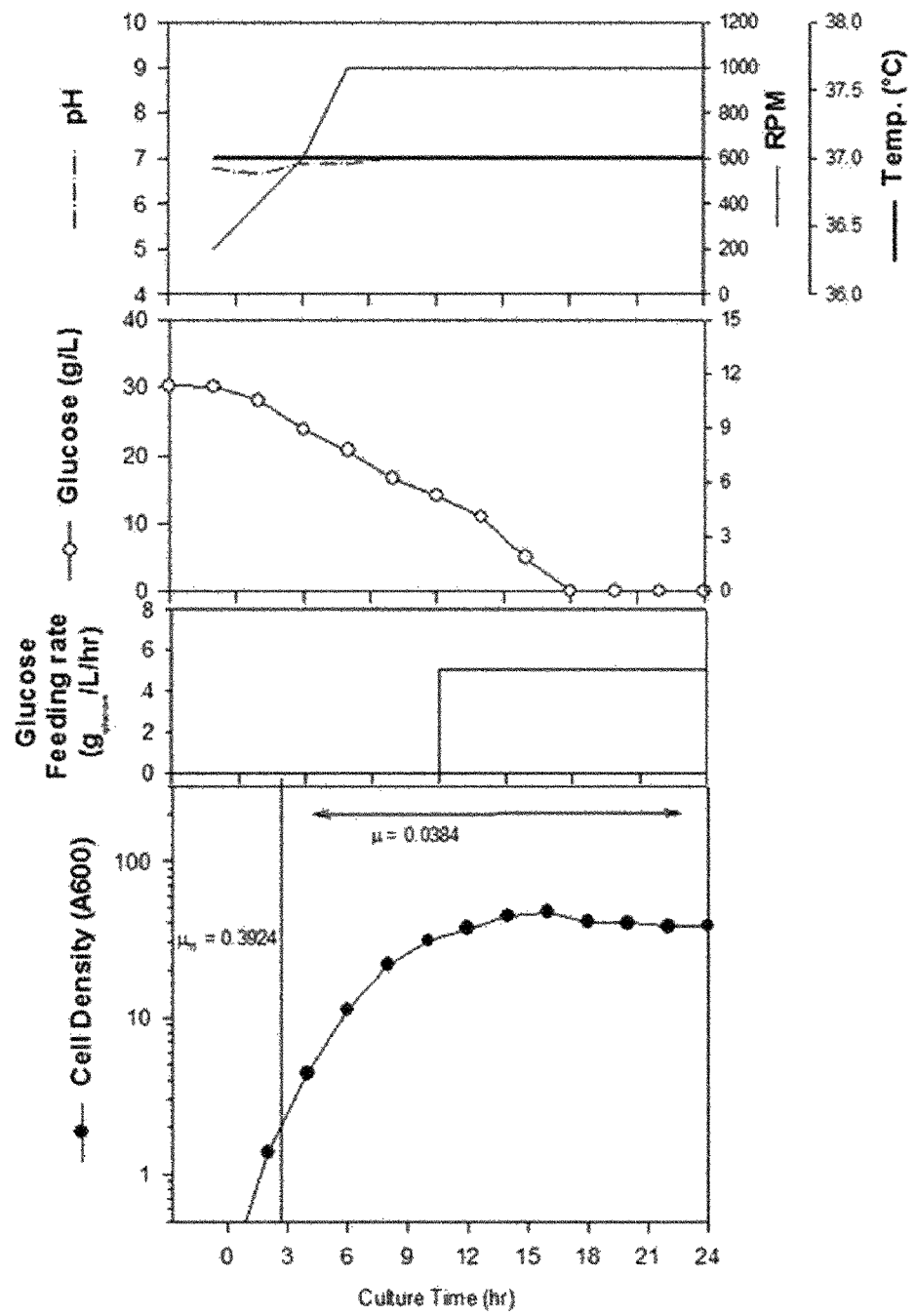
FIG. 15 is graphs showing fermentation of E. coli, which is transformed into pACYCWG-BcAT vector in a strain-enhanced experiment according to an embodiment of the present invention.
Figure 16:
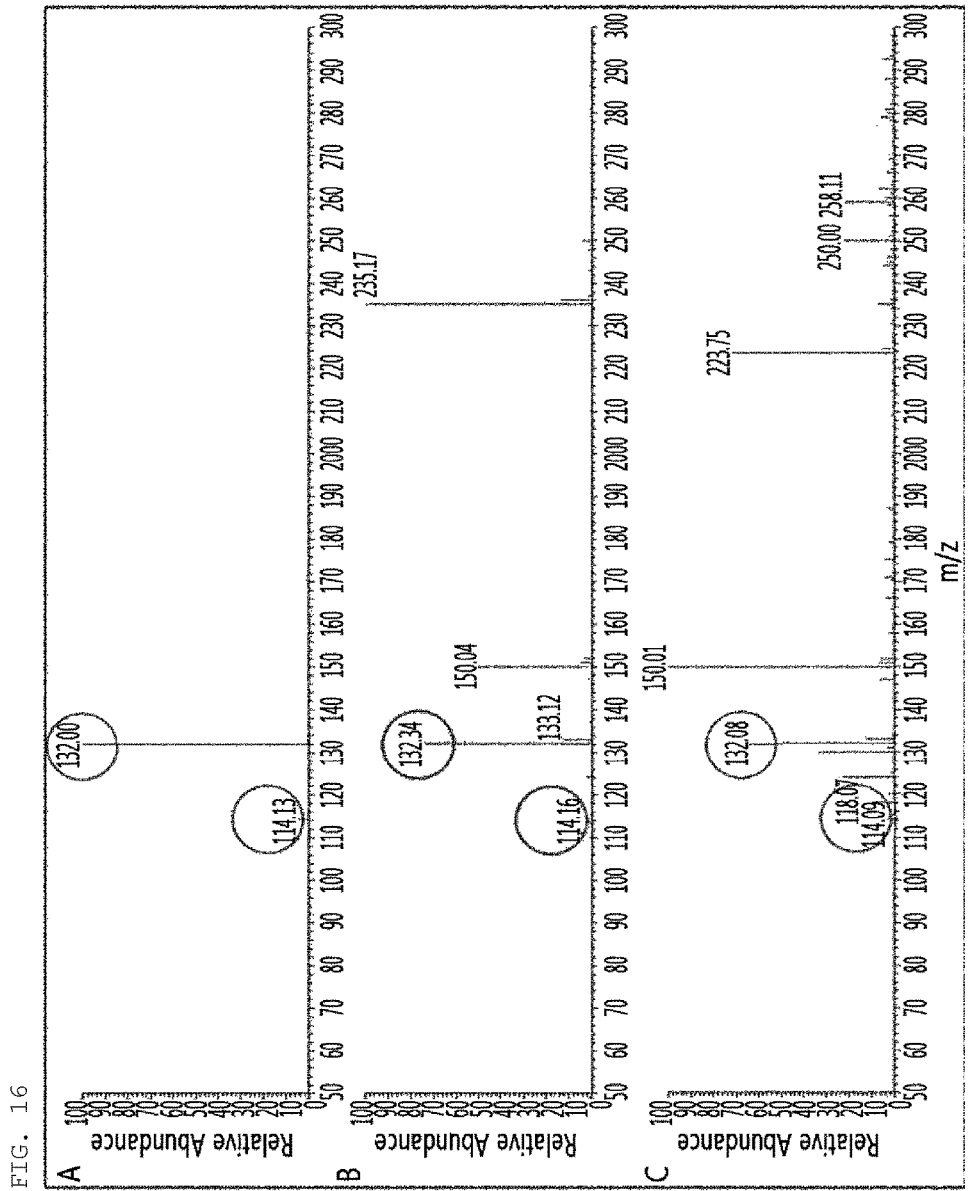
FIG. 16 is graphs showing LC-MS results of biosynthetic activity of 6-aminocaproic acid by culturing E. coli in the strain-enhanced experiment according to an embodiment of the present invention, followed by obtaining a supernatant.

A strain HMS174(DE3), in which RecA gene encoding recombinase was mutated, was selected and used because of the possibility that recombination might occur in the strain, as the size of the vector is huge.

pPKNI was transformed into the strain HMS174(DE3), and the production of 6-ACA was induced by fermentation. Specifically, in 2.5 L of medium containing the components shown in Table 12, *E. coli* was cultured for 24 hours. 3 hours after the culturing, 0.4 mM of IPTG was added to induce the expression of enzymes, and 5 g/L of glucose was fed after all of the initial glucose was consumed (FIG. 15). After the culturing of *E. coli*, the supernatant was obtained and analyzed by LC-MS/MS. As a result, it was confirmed that 6-aminocaproic acid was produced (FIG. 16).

The invention claimed is:

1. A method for preparing 6-aminocaproic acid comprising:
   preparing an expression vector comprising
   HpaI (4-hydroxy-2-oxoheptane-1,7-dioate aldolase)-HpaH (2-oxohept-3-ene-1,7-dioate dehydratase) gene comprising the polynucleotide of SEQ ID NO: 3,
   nemA (N-ethylmaleimide reductase) gene comprising the polynucleotide of SEQ ID NO: 4,
   KIVD (alpha-ketoisovalerate decarboxylase) gene comprising the polynucleotide of SEQ ID NO: 5; and
   at least one of PdAT (beta-alanine-pyruvate transaminase) gene comprising the polynucleotide of SEQ ID NO: 6 and BcAT (adenosylmethionine-8-amino-7-oxononanoate aminotransferase) gene comprising the polynucleotide of SEQ ID NO: 7; and
   transforming the expression vector into a microorganism.

2. The method of claim 1, wherein the expression vector further comprises nucleic acid (polynucleotide) sequences encoding GST, MBP, NusA, thioredoxin, ubiquitin, FLAG, BAP, 6HIS, STREP, CBP, CBD, or S-tag affinity tag.

3. The method of claim 1, wherein the expression vector further comprises nucleic acid sequences encoding kex2p in yeasts, purine in mammals, Factor Xa, enterokinase, subtilisin, tobacco etch virus protease, thrombin, or ubiquitin hydrolase.

4. The method of claim 1, wherein the microorganism is a bacterium, yeast, or fungus.

5. The method of claim 1, wherein the method further comprises producing and secreting 6-aminocaproic acid by culturing the transformed microorganism in a fed-batch fermentation.

6. The method of claim 5, wherein the method further comprises purifying protein secreted.

7. An expression vector for biosynthesis of 6-aminocaproic acid comprising
   HpaI (4-hydroxy-2-oxoheptane-1,7-dioate aldolase)-HpaH (2-oxohept-3-ene-1,7-dioate dehydratase) gene comprising the polynucleotide of SEQ ID NO: 3,
   nemA (N-ethylmaleimide reductase) gene comprising the polynucleotide of SEQ ID NO: 4,
   KIVD (alpha-ketoisovalerate decarboxylase) gene comprising the polynucleotide of SEQ ID NO: 5; and
   at least one of PdAT (beta-alanine-pyruvate transaminase) gene comprising the polynucleotide of SEQ ID NO: 6 and BcAT (adenosylmethionine-8-amino-7-oxononanoate aminotransferase) gene comprising the polynucleotide of SEQ ID NO: 7.

8. The expression vector of claim 7, wherein the expression vector is pACYCWG shown in FIG. 2.

9. A transformant which is transformed with the expression vector of claim 7.

10. The transformant of claim 9, wherein the transformant is a bacterium, yeast, or fungus.

11. The transformant of claim 9, wherein the transformant transforms pyruvate and/or succinic semialdehyde (SSA) into 6-aminocaproic acid.

12. A method for producing caprolactam further comprises transforming 6-aminocaproic acid produced by the method according to claim 1 into caprolactam.

13. A transformant which is transformed with the expression vector of claim 6.

14. The transformant of claim 13, wherein the transformant is a bacterium, yeast, or fungus.

15. The transformant of claim 13, wherein the transformant transforms pyruvate and/or succinic semialdehyde (SSA) into 6-aminocaproic acid.

16. The method of claim 1, wherein the microorganism is *E. coli*.

17. The transformant of claim 9, wherein the transformant is *E. coli*.

* * * * *